US007305347B1

(12) United States Patent
Joao

(10) Patent No.: US 7,305,347 B1
(45) Date of Patent: Dec. 4, 2007

(54) APPARATUS AND METHOD FOR PROVIDING EMPLOYEE BENEFITS AND /OR EMPLOYEE BENEFITS INFORMATION

(76) Inventor: Raymond Anthony Joao, 122 Bellevue Pl., Yonkers, NY (US) 10703

( * ) Notice: Subject to any disclaimer, the term of this patent is extended or adjusted under 35 U.S.C. 154(b) by 0 days.

(21) Appl. No.: 09/391,335

(22) Filed: Sep. 7, 1999

Related U.S. Application Data

(60) Provisional application No. 60/100,651, filed on Sep. 16, 1998, provisional application No. 60/099,653, filed on Sep. 9, 1998.

(51) Int. Cl.
*G06Q 99/00* (2006.01)
(52) U.S. Cl. .................. 705/1; 705/4; 705/35
(58) Field of Classification Search ............... 705/2–4, 705/35, 36, 1
See application file for complete search history.

(56) References Cited

U.S. PATENT DOCUMENTS

| | | | |
|---|---|---|---|
| 4,648,037 A * | 3/1987 | Valentino | 705/36 R |
| 4,750,121 A | 6/1988 | Halley et al. | |
| 4,965,763 A | 10/1990 | Zamora | |
| 4,969,094 A | 11/1990 | Halley et al. | |
| 5,121,994 A | 6/1992 | Molitoris | |
| 5,191,522 A * | 3/1993 | Bosco et al. | 705/4 |
| 5,220,500 A | 6/1993 | Baird et al. | |
| 5,244,296 A | 9/1993 | Jensen | |
| 5,429,506 A | 7/1995 | Brophy et al. | |
| 5,537,618 A | 7/1996 | Boulton et al. | |
| 5,566,291 A | 10/1996 | Boulton et al. | |
| 5,590,037 A | 12/1996 | Ryan et al. | |
| 5,600,554 A * | 2/1997 | Williams | 705/1 |
| 5,630,073 A | 5/1997 | Nolan | |
| 5,652,842 A | 7/1997 | Siegrist, Jr. et al. | |
| 5,737,539 A | 4/1998 | Edelson et al. | |
| 5,787,453 A | 7/1998 | Kennedy | |
| 5,802,500 A | 9/1998 | Ryan et al. | |
| 5,806,042 A | 9/1998 | Kelly et al. | |
| 5,845,255 A | 12/1998 | Mayaud | |

(Continued)

FOREIGN PATENT DOCUMENTS

WO WO 99/05625 A1 * 4/1999

OTHER PUBLICATIONS

Anonymous, "Edify Broadens Application Suites in New Release of Employee Service System", PR Newswire, Jun. 30, 1998, 3 pages.*

(Continued)

*Primary Examiner*—C. Luke Gilligan
(74) *Attorney, Agent, or Firm*—Raymond A. Joao, Esq.

(57) ABSTRACT

A computer-implemented method, including receiving a request or claim for an employee benefit via, on, or over, the Internet and/or World Wide Web, processing the request or claim for an employee benefit with a first processing device or a second processing device accessed via, on, or over, or which operates on or over, the Internet and/or World Wide Web, determining with the first processing device or with the second processing device whether the employee benefit requested in the request or claim for an employee benefit is to be provided, generating a message in response to the request or claim for an employee benefit, and transmitting the message to a communication device associated with at least one of the employee, the benefit beneficiary, an employer, and a benefit administrator, via, on, or over, the Internet and/or World Wide Web.

238 Claims, 4 Drawing Sheets

U.S. PATENT DOCUMENTS

| | | | |
|---|---|---|---|
| 5,852,824 A | 12/1998 | Brown | |
| 5,864,822 A * | 1/1999 | Baker, III | 705/14 |
| 5,867,821 A | 2/1999 | Ballantyne et al. | |
| 5,878,337 A | 3/1999 | Joao et al. | |
| 5,878,405 A | 3/1999 | Grant et al. | |
| 5,897,649 A | 4/1999 | Kennedy | |
| 5,903,830 A | 5/1999 | Joao et al. | |
| 5,913,029 A | 6/1999 | Shostak | |
| 5,913,198 A * | 6/1999 | Banks | 705/4 |
| 5,919,151 A | 7/1999 | Gustafson | |
| 5,926,792 A | 7/1999 | Koppes et al. | |
| 5,930,759 A * | 7/1999 | Moore et al. | 705/2 |
| 5,960,407 A | 9/1999 | Vivona | |
| 5,961,332 A | 10/1999 | Joao | |
| 5,970,463 A | 10/1999 | Cave et al. | |
| 5,974,389 A | 10/1999 | Clark et al. | |
| 5,976,058 A | 11/1999 | Gustafson | |
| 5,978,811 A | 11/1999 | Smiley | |
| 5,991,741 A | 11/1999 | Speakman et al. | |
| 5,991,744 A | 11/1999 | DiCresce | |
| 5,999,917 A | 12/1999 | Facciani et al. | |
| 6,014,629 A | 1/2000 | DeBruin-Ashton | |
| 6,014,642 A | 1/2000 | El-Kadi et al. | |
| 6,041,313 A * | 3/2000 | Gilbert et al. | 705/36 |
| 6,047,270 A | 4/2000 | Joao et al. | |
| 6,067,522 A * | 5/2000 | Warady | 705/2 |
| 6,073,106 A | 6/2000 | Rozen et al. | |
| 6,076,066 A * | 6/2000 | DiRienzo et al. | 705/4 |
| 6,090,044 A | 7/2000 | Bishop et al. | |
| 6,092,047 A | 7/2000 | Hyman et al. | |
| 6,161,096 A | 12/2000 | Bell | |
| 6,192,346 B1 * | 2/2001 | Green | 705/9 |
| 6,205,434 B1 | 3/2001 | Ryan et al. | |
| 6,208,973 B1 * | 3/2001 | Boyer et al. | 705/2 |
| 6,216,104 B1 | 4/2001 | Moshfeghi et al. | |
| 6,217,536 B1 | 4/2001 | Gustafson | |
| 6,235,176 B1 | 5/2001 | Schoen et al. | |
| 6,263,341 B1 | 7/2001 | Smiley | |
| 6,283,761 B1 | 9/2001 | Joao | |
| 6,302,844 B1 | 10/2001 | Walker et al. | |
| 6,324,437 B1 | 11/2001 | Frankel et al. | |
| 6,338,097 B1 | 1/2002 | Krenzke et al. | |
| 6,341,265 B1 * | 1/2002 | Provost et al. | 705/4 |
| 6,343,271 B1 * | 1/2002 | Peterson et al. | 705/4 |
| 6,345,260 B1 | 2/2002 | Cummings, Jr. et al. | |
| 6,356,909 B1 | 3/2002 | Spencer | |
| 6,363,394 B1 | 3/2002 | Rajarajan et al. | |
| 6,393,404 B2 | 5/2002 | Waters et al. | |
| 6,401,079 B1 | 6/2002 | Kahn et al. | |
| 6,411,939 B1 | 6/2002 | Parsons | |
| 6,473,500 B1 | 10/2002 | Risafi et al. | |
| 6,529,725 B1 | 3/2003 | Joao et al. | |
| 6,604,080 B1 | 8/2003 | Kern | |
| 6,609,111 B1 | 8/2003 | Bell | |
| 6,654,786 B1 * | 11/2003 | Fox et al. | 709/203 |
| 6,662,194 B1 | 12/2003 | Joao | |
| 6,804,656 B1 | 10/2004 | Rosenfeld et al. | |
| 2002/0013751 A1 | 1/2002 | Facciani et al. | |
| 2002/0069077 A1 | 6/2002 | Brophy et al. | |
| 2003/0001005 A1 | 1/2003 | Risafi et al. | |
| 2003/0053609 A1 | 3/2003 | Risafi et al. | |

OTHER PUBLICATIONS

Meade, Jim, "A low-cost alternative to the traditional HRIS", HRMagazine, Aug. 1998, vol. 43, No. 9, pp. 37-40.*

Anonymous, "Employease Opens Four New Offices", Business Wire, Business Editors & Technology/Insurance Writers, Apr. 9, 1998, 3 pages.*

Greengard, Samuel, "Extranets: The Latest developments", Workforce, Mar. 1997, vol. 76, No. 3, pp. 93-94.*

Coleman, David I., "Managing health benefits: The birth of an on-line age", Business and Health, Jan. 1997, vol. 15, No. 1, pp. 30-38.*

Asinof, Lynn, "Click & Shift: Workers Control Their Benefits On-Line", Wall Street Journal, Nov. 21, 1997, p. C1.*

Greengard, Samuel, "When HRMS goes global: Managing the data highway", Personnel Journal, Jun. 1995, vol. 74, No. 6, p. 90.*

"Information found on the website of E-Benefits", Dec. 1997, 5 pages.*

Nacinovich, Mark, "Web-based HR software trickles down", Accounting Technology, Aug. 1998, vol. 14, No. 7, p. 45.*

Greengard, Samuel, "Building a self-service culture that works", Workforce, Jul. 1998, vol. 77, No. 7, p. 60.*

Secrist, Intelligent messaging system notifies plant personnel, Feb. 1997, Control Engineering, pp. 27-28.*

AT&T Spinoff of Lucent Impacts Benefit Obligations, Aug. 1997, Employee Benefit Plan Review, p. 51.*

Koco, Portability now in many employee benefit plans, Sep. 1995, National Underwriter, vol. 99 No. 38, p. 24.*

Ulrich, Shared services: From vogue to value, 1995, HR. Human Resource Planning, pp. 12-24.* http://www.employease.com via http://web.archive.org, available Feb. 1997, downloaded Oct. 2002.*

Vizard, N.Y. saves big with client/server, Mar. 1993, Computerworld, pp. 87-89.*

Foster, Portability of pension benefits among jobs, Jul. 1994, Monthly Labor Review, pp. 45-50.*

Rogers, What's new, Jun. 1996, HRMagazine, vol. 41 Issue 6.*

Leslie L. Lesnick, et al., Creating Cool Intelligent Agents for the Net, 1997, IDG Books Worldwide, Inc. U.S.A.

Alper Caglayan, et al., Agent Sourcebook a Complete Guide to Desktop, Internet, and Intranet Agents, 1997, Wiley, U.S.A.

Jerry S. Rosenbloom, The Handbook of Employee Benefits, 1996, McGraw-Hill, U.S.A.

* cited by examiner

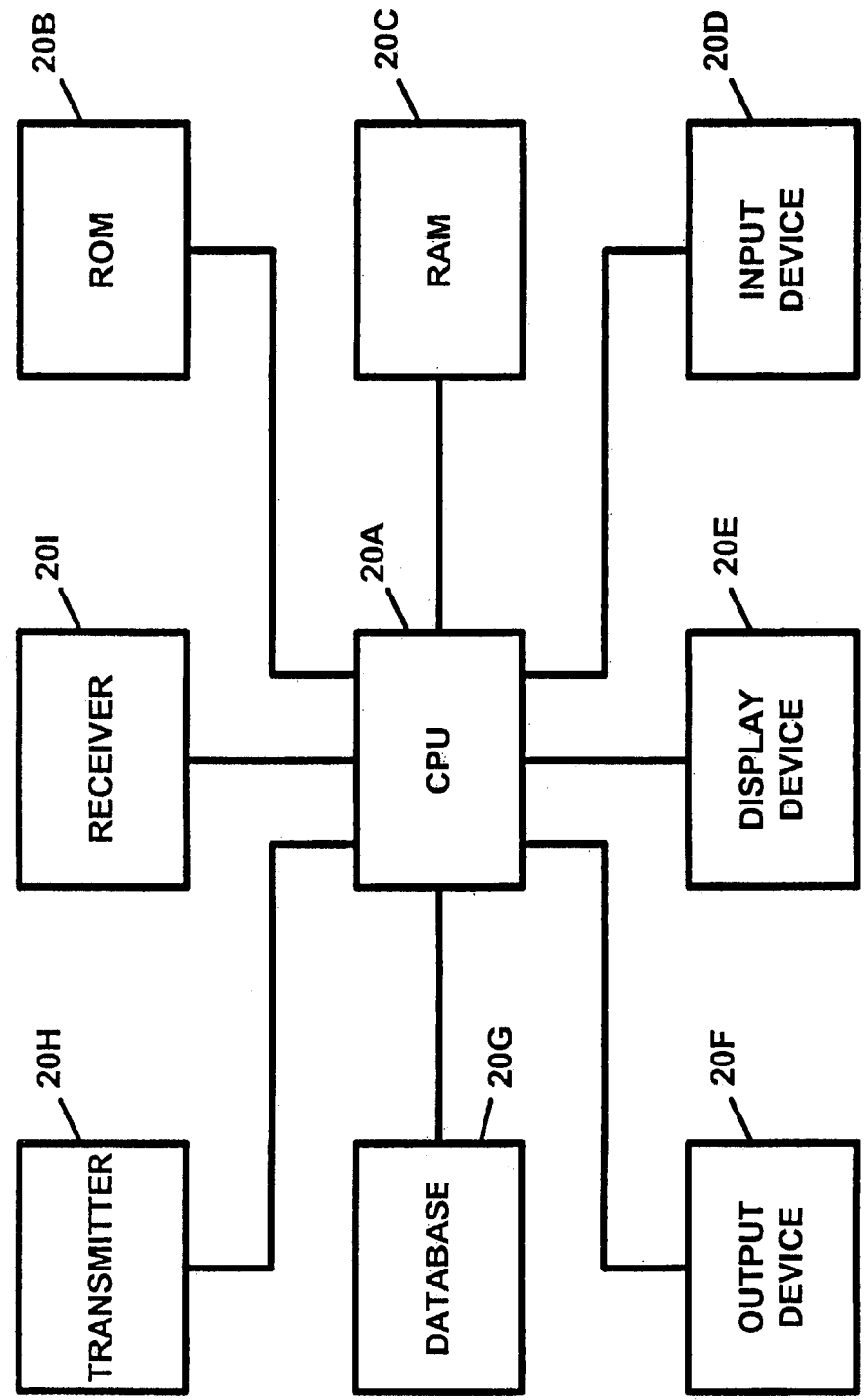

APPARATUS AND METHOD FOR PROVIDING EMPLOYEE BENEFITS AND /OR EMPLOYEE BENEFITS INFORMATION

RELATED APPLICATIONS

Applicant hereby claims the priority of U.S. Provisional Patent Application Ser. No. 60/099,653, filed Sep. 9, 1998, entitled Apparatus and Method For Providing Employee Benefits And/Or Employee Benefits Information. Applicant also hereby claims the priority of U.S. Provisional Patent Application Ser. No. 60/100,651 filed Sep. 16, 1998, entitled Apparatus and Method For Providing Employee Benefits And/Or Employee Benefits Information.

FIELD OF THE INVENTION

The present invention is directed to an apparatus and a method for providing employee benefits and/or employee benefits information and, in particular, to an apparatus and a method for providing employee benefits and/or employee benefits information in a network environment.

BACKGROUND OF THE INVENTION

Many employers provide employee benefits, in the form of various benefits, plans and programs (hereinafter referred to as "benefits"), to their employees as part of their total compensation packages. These benefits may include employer provided personnel benefits, health insurance benefits, disability insurance benefits, life insurance benefits, pension benefits, retirement benefits, stock option programs, profit sharing programs, employee savings accounts and plans, employee credit union accounts and services, employee discount programs, and other valuable benefits and programs. The list can go on to include other employer-specific or industry-specific benefits.

Oftentimes, the benefits which are provided to employees are so numerous and complex in understanding how to take advantage of them, that the employee may not be aware of them or know how to take advantage of them. In other instances, the providers of the benefits may be difficult to deal with or may not be easily accessible to the employee. In these instances, the employee will have to expend efforts and time, sometimes amounting to great efforts and a great deal of time, in order to obtain a benefit or information about a benefit.

Frustration may result when benefits may be too difficult or complicated to obtain or to gain access to, especially when benefits are not easily understood or when benefits providers are difficult to deal with or to communicate with. Given the fact that most employees seek benefits during the workday, company or employer time and resources are expended by the employee in attending to benefits matters, usually at the employer's expense.

The offering and the administration of employee benefits typically requires that a vast amount of diverse and complex information be managed, administered, and be constantly monitored by administrators. Employees must also be assisted in their efforts to claim or gain access to their benefits and/or to information related thereto.

The administration of employee benefits and benefits plans and programs also requires that competent administrators be employed by the employer in order to administer and oversee these programs. These administrators typically provide administrative and managerial services and often must interact with the various benefits providers in order to ensure that the providers comply with their obligations under the plans or programs. Administrators must also keep the employees appraised of changes to, and/or the status of, these benefits.

The administrators must also deal with instances when employees have difficulty in obtaining benefits and/or benefit information. Administrators must also deal with other benefits-related issues as they arise.

As can be easily seen, great amounts of time, money and resources are expended in offering and administering an employee benefits plan or program. Even greater amounts are expended when benefits and/or benefits information are not readily available to, or accessible by, the employee.

Even when administrators do their jobs well, the typically large ratios of employees to administrators can oftentimes hinder the ability of employees to receive all of the information and/or assistance they might need in order to obtain benefits, obtain benefits information, or to resolve difficulties in dealing with benefits providers.

Employees who may have to expend unnecessary amounts of time and energy, during the working day and/or while on company time, in seeking benefits and/or benefits information which should otherwise be easily and readily available to them.

The above described characteristics of typical employee benefits plans and programs can result in great costs to employers in the form of monetary costs, company resources being inefficiently utilized and in less than optimal output from employees.

SUMMARY OF THE INVENTION

The present invention provides an apparatus and a method for providing employee benefits and/or employee benefits information to employees and administrators which overcomes the shortcomings of the prior art. The apparatus and method of the present invention provides employees and administrators of benefit plans or programs with access to employee benefits or benefits information in a network environment. The present invention provides benefits or benefits information in an easy and efficient manner, thereby minimizing the time, expense, and effort required in obtaining employee benefits and/or employee benefits information.

The present invention also provides an apparatus and a method for allowing an employee or benefits administrator to communicate with, and transact benefits-related business with, the respective employer and/or with any of the various benefits providers.

The present invention provides an apparatus and a method for providing employee benefits and/or employee benefits information by providing access to a centralized processing computer system which is linked with computer systems for, or associated with, each of the benefits providers. The employee or benefits administrator can access the centralized processing computer system with a communication device such as a personal computer, a computer stationed at a kiosk at the employer's location and/or at any other public, semi-public, or private location and/or any other suitable communication device.

The employee or administrator may obtain benefit information from the centralized processing computer system as well as obtain information from, or communicate and/or transact benefits-related business with, any of the providers which are associated with the employee benefits plan or program via the centralized processing computer system.

The employee benefits and/or employee benefit plans or programs can include employee personnel information including wage, salary and payroll information and status, vacation time, sick time and personal time information and status, tuition reimbursement and/or continuing education programs, health insurance plans or programs, life insurance plans or programs, disability insurance plans or programs, employee savings plans and programs, employee retirement plans and programs, employee pension benefits or programs and status of same, employee credit union accounts, plans or programs, employee savings and employee loan plans or programs, and various employee discount plans and programs. The central processing computer system can contain, or provide links to, any other employee benefits and/or information related thereto.

The information regarding employee benefits for each employee participating in a plan or program can be stored in a database or in a collection of databases. Information can also be stored in a database or in a collection of databases at each of the respective benefits providers computers. The information from each benefit provider can be updated in real-time via dynamically linked database techniques and/or by utilizing other database management techniques.

The apparatus includes a central processing computer system or server computer for receiving and storing the pertinent information and/or information which provides a link or links to benefits information for the various benefits providers and sources. The apparatus also includes an employer computer which is linked with the central processing computer system and which provides all pertinent employee and employer information, as well as employer provided benefits and programs.

The employer information can also include information regarding the various benefits providers, such as, for example, health insurance benefits and providers, disability insurance benefits and providers, life insurance benefits and providers, credit union benefits and providers, pension fund benefits and providers, retirement benefits and providers, various employee discount and buying service benefits and providers, as well as any other benefits and/or benefits programs which are, or which may be, provided under, or in connection with, the employment relationship.

The apparatus also includes a health insurance computer system, associated with each health insurance provider, which is also linked to the central processing computer system. Each of the various health insurance providers can have a computer associated therewith for providing information, related to their respective benefits or plans, to the central processing computer system.

The apparatus also includes a disability insurance computer system associated with each disability insurance provider, which is also linked with the central processing computer system. Each of the various health insurance providers can have a computer associated therewith for providing information, related to their respective benefits or plans, to the central processing computer system.

The apparatus also includes a life insurance computer system, associated with each life insurance provider, which is also linked to the central processing computer system. Each of the various life insurance providers can have a computer associated therewith for providing information, related to their respective benefits or plans, to the central processing computer system.

The apparatus also includes a credit union or banking services computer system, associated with each credit union or banking services provider, which is also linked to the central processing computer system. The credit union or banking services computer system(s) can provide information concerning the employee's savings accounts, loan information, mortgage information, as well as information concerning other benefits which are available to the employee, such as savings interest rates, loan and mortgage rates which are available to the employee as well as any other financial information concerning the employee's benefits which are, or which may be, offered by credit union or bank(s) associated with the employee benefits plan or program.

The apparatus also includes a pension benefits computer system, associated with each pension benefits provider, which is also linked to the central processing computer system and which provides pension benefits information regarding employee pension accounts to the central processing computer system.

The apparatus also includes a financial/retirement benefits computer system, associated with each financial/retirement benefits provider, which is also linked to the central processing computer system for providing information regarding employee retirement accounts and/or retirement account benefits and/or information to the central processing computer system.

The apparatus also includes an employee discount or buying service computer system, associated with each employee discount and/or buying service provider, which is also linked to the central processing computer system. The employee discount or buying service computer system provides benefits information regarding employee discount and/or buying service benefits and/or information to the central processing computer system. An employee discount computer system may be associated with each of the providers of employee discounts and/or buying services which are provided under the employee benefits plan or program.

The apparatus also includes a communication device such as a personal computer, a desktop computer system, or any other suitable computer system or communication device which is, or which can be, linked to the central processing computer system. The communication device can be utilized by the employee or administrator in order to access the central processing computer system in order to obtain benefits, obtain benefits information, correspond or communicate with, and transact benefits-related business with, the employer, insurance providers, financial institutions, discount providers and/or any other benefits providers described herein. The communication device can access and interact with the central processing computer system along the computer systems of any of the benefits providers described herein.

The apparatus and method of the present invention can be utilized on, or over, any communication network as well as on, or over the Internet, the World Wide Web, internets, intranets, local area networks (LANs), wide area networks (WANs), as well as any other communication system or network.

Any and all communications and data and/or information transfer which can be performed in conjunction with the use of the apparatus and methods of the present invention can be encrypted, so as to provide a secure communications environment, by utilizing any of the known encryption and/or other security methods and/or techniques.

The present invention provides an apparatus and a method for allowing the employee or administrator to access or obtain benefits and/or benefits information, from any location and at any time of day or night.

The employee or administrator can correspond with his or her employer and with any of the various benefits providers described herein via the apparatus such as by electronic mail correspondence, facsimile correspondence, electronic form submission or transmission, and/or by any other suitable electronic communication method or technique.

The present invention can be utilized in order to allow employees to purchase enhanced or upgraded benefits, downgrade benefits, and/or exchange benefits for other benefits, so as to allow the employee to custom tailor benefits packages so as to fit their needs.

The present invention also allows employees to correspond directly with the respective benefits providers in order to effect benefits changes as desired. This ability to allow the employees to access their providers directly, with such access being provided to large numbers of individual employees, provide for more personalized relationships between individual employees and their benefits providers, as well as provide for employee/benefits provider relationships which may be maintained in the future.

The present invention can provide notification of an employee's action to upgrade or change any of the benefits described herein so as to keep the employer informed about the status of benefits for each of its employees. Each of the benefits providers which are serviced by the apparatus of the present invention can also be provided with lists of employees covered under the various plans serviced by the apparatus along with the benefits provided to those employees.

The present invention can also provide benefits providers with information regarding employees who have recently upgraded benefits and/or which have taken advantage of benefits offers, employee discounts and/or buying services thereby providing the respective benefits providers with information and/or employees with whom the provider may communicate futures offerings.

The apparatus and method of the present invention can also provide an employee with the ability to select a different benefits provider from whom the employee can obtain benefits. The present invention can also be utilized in order for an employee to utilize monies and/or credits, which can be provided by their respective employer for benefits under the employment relationship, in order to select and obtain a benefits plan or program which is tailored to the employee's needs and/or desires.

By allowing an employee to obtain a benefits plan or program, which is independent of the employer, the present invention can be utilized in order to provide individual benefits accounts which can be portable so that the individual employee may take his or her benefits plan or program from job to job and/or retain his benefits through periods of unemployment, in retirement and/or in periods between jobs.

The present invention can also provide informational services, related to employee benefits, to the employee or administrator in various areas, including law, medicine, dentistry, accounting, and tax planning, etc.

The present invention also provides an apparatus and method for facilitating communication between various benefits providers. The present invention can also be utilized to allow various providers, such as doctors, physicians and other healthcare providers to confer and share information about an employee. In instances when an employee may need an authorized referral for a physician or other healthcare provider, the authorized referral may be provided from the referring provider to the referred to provider via the communication system and apparatus of the present invention. In this manner, referrals can be documented by the apparatus of the present invention for insurance purposes.

The central processing computer system can be associated with, and/or be utilized by, a benefits providing institution and/or a benefits management institution in order to provide the services described herein. The central processing computer system can also be utilized by brokers and/or dealers of the various employee benefits, insurance plans or programs, pension plans or programs, retirement plans or programs, employee discount and/or buying services plans or programs, etc., which are described herein.

The present invention can be utilized in conjunction intelligent agents, software agents and/or mobile agents.

Applicant hereby incorporates by reference herein the subject matter of the *Agent Sourcebook, A Complete Guide to Desktop, Internet and Intranet Agents*, by Alper Caglayan and Colin Harrison, Wiley Computer Publishing, 1997 Applicant also incorporates by reference herein the subject matter of *Cool Intelligent Agents For The Net*, by Leslie L. Lesnick with Ralph E. Moore, IDG Books Worldwide, Inc. 1997.

Intelligent agents can be utilized in any of the embodiments described herein in order to obtain information for an employee, an administrator or any of the various providers described herein.

An intelligent agent can act on behalf of the employee to obtain information on benefits and/or benefits information availability, status of benefits, status of benefits claims, and information about benefits providers, etc. An intelligent agent(s) can also be empowered to act for the employee or administrator so as to request benefits and/or benefits information, request services, purchase or order benefits and/or goods and/or services provided via the benefits plan or program.

An intelligent agent(s) can be programmed to perform any action and/or activity described herein for, or on behalf of, the employee, the administrator, any of the various benefits providers, and the entity operation the central processing computer system. An intelligent agent can also be programmed to report the results of its findings and/or its actions taken to the respective employee, administrator, or benefits provider.

The employee, or administrator, may utilize an intelligent agent in order to find, locate and/or obtain employee benefits and/or employee benefits information by requesting and/or instructing an intelligent agent(s) to do so. The employee may also request or instruct an intelligent agent to find, locate and/or obtain information regarding his or her employment status and benefits which are provided to the employee. The employee may request and/or instruct an intelligent agent to find, locate and/or obtain information, instructions and/or explanations regarding benefits, instructions for obtaining and claiming benefits.

The employee or administrator may utilize and/or deploy an intelligent agent(s) at any time and from any location.

The intelligent agent(s) can be deployed from the communication device, from the central processing computer system, or from any of the benefits providers computer systems.

The employee or administration can also utilize and/or deploy an intelligent agent(s) in order to obtain any employee benefits and/or employee benefits information, submit changes to benefits, submit benefits claims, register and/or subscribe to any of the employee benefits described herein, and/or make inquiries and/or status inquiries regarding employee benefits and/or employee benefits claims.

The employee can also utilize an intelligent agent(s) in order to transmit messages to the employer via e-mail transmission, facsimile transmission, electronic form submission or transmission, and/or by any other communication means, in order to allow the employee make changes to any of his or her employee benefits.

The employee can also utilize an intelligent agent(s) in order to effect any changes and/or modifications to any of the data and/or information described herein, on-line via the communication device.

The employee or administrator can utilize an intelligent agent(s) which can be dedicated to each provider or coverage type and which can obtain detailed explanations of the coverage and/or benefits provided, applicable deductibles or co-payments under the plan, instructions for obtaining benefits and/or directories and/or listings of providers, etc.

The employee can also utilize an intelligent agent(s) in order to select a primary care provider, if applicable, for each of the various benefits provided. The employee can also utilize an intelligent agent(s) in order to change primary care provider(s) and to request referral authorizations for specialists. The employee can also utilize intelligent agent(s) in order to submit claims on-line and check the status of claims which are pending.

The employee may also utilize an intelligent agent(s) in order to communicate directly with the health care benefits provider(s). The employee can also utilize an intelligent agent(s) in order to purchase upgraded benefits and/or change coverages, directly from the benefits provider, on-line via the communication device 20, in order to receive enhanced and/or upgraded benefits.

The employee or administrator can utilize an intelligent agent(s) in order to obtain detailed explanations of the benefits provided, instructions and/or information for obtaining and/or claiming benefits, information regarding filing a disability insurance claim, applicable deductibles and/or co-payments under the plan, directories and/or listings of individuals, doctors and/or other individuals and/or entities which have to be notified and/or contacted in order to file a disability insurance claim.

The employee may also utilize an intelligent agent(s) in order to change and/or modify their benefits as well as to search for more attractive benefits. An intelligent agent(s) can also be utilized in order to select and/or obtain a custom-tailored benefits package for an employee and/or for an entire organization.

In all of the herein described embodiments, the employee or administrator can communicate or correspond with the central processing computer system and/or any of the respective provider computer systems by utilizing an intelligent agent(s).

An intelligent agent(s) can also be utilized in order to pool employees from different employers together in order to provide preferred group rates for complete benefit plans or programs as well any single provider benefits or coverage. In these instances, an intelligent agent(s) may be utilized and/or deployed by an employee, by employers, the operator of the central processing computer system, and/or by any of the providers and/or provider types described herein.

Benefits providers can utilize an intelligent agent(s) in order to communicate new programs, new benefits, and/or special programs and/or benefits discount offerings, to the employees who are serviced by the present invention. In this manner, benefits providers can offer or sell their respective services, policies and/or goods to the employees and/or to administrators.

In any of the here-described embodiments, an intelligent agent(s) can be deployed from the communication device and/or from any of the respective provider computer systems. The operator of the central processing computer system can also utilize an intelligent agent(s) in order to perform information retrieval, information processing, and/or communication with employees, administrators and/or any of the benefits providers and/or benefits providers types described herein.

The employee, administrator, benefits provider, and/or central processing computer system operator, can request and/or instruct the intelligent agent(s) to perform a task and/or obtain information. The intelligent agent(s) will them be deployed to perform its task. Once the intelligent agent(s) has completed the task, the intelligent agent(s) can report the fact that the task has been completed, as well as the result(s) and/or outcome(s) of the task, along with any information related thereto, to the respective employee, administrator, benefits provider, and/or central processing computer system operator, on whose behalf the intelligent agent(s) acted.

The present invention can be utilized to provide employee benefits and/or employee benefits information for a number of, or for a plurality of, employers and employees.

The present invention can allow employees to maintain and continue their relationships with their respective benefits providers even after the employment relationship, which brought the employee to the benefits provider, may cease to exist. In this manner, the present invention provides employees with the opportunity to continue certain, or all of, their employment benefits with any of the benefits providers, in spite of changes in employment, and/or changes in employment status.

In this manner, the relationships between employees and the respective benefits providers will facilitate the creation of individual benefits accounts which will provide employees with greater independence in selecting and maintaining employee benefits while providing continuation of benefits and/or benefits stability, regardless of their employer and/or employment status.

The present invention can also be utilized as a clearinghouse for the buying and selling of employee benefits. The present invention can also be utilized to provide notification of changes and/or modifications to employee benefits. The present invention can also be utilized for providing notification of requests for, and/or offerings of, employee benefits.

The present invention can also be utilized to provide for the management and/or administration of financial accounts for any of the respective parties utilizing the apparatus and method of the present invention. The present invention can also be utilized to effectuate and/or execute financial transactions for, and/or on behalf of, a party utilizing the present invention.

The present invention can also provide notification of financial transactions which occur on, and/or in conjunction with, financial accounts. The present invention can also provide notification of benefits transactions and/or transactions involving benefits and/or benefits accounts.

The present invention can also provide for the authentication of, and/or for electronic and/or digital signatures, which can be utilized in conjunction with any and/or all of the various forms, transmissions, and/or communications, which are described herein as being utilized for providing communication between any of the parties described herein.

Accordingly, it is an object of the present invention to provide an apparatus and a method for providing employee benefits and/or employee benefits information.

It is another object of the present invention to provide an apparatus and a method for providing employee benefits and/or employee benefits information over a communication network.

It is yet another object of the present invention to provide an apparatus and a method for providing employee benefits and/or employee benefits information by accessing same from a centralized processing computer system or other centralized information source.

It is still another object of the present invention to provide an apparatus and a method for providing access to employee benefits and/or employee benefits information for a comprehensive and/or integrated employee benefits package, plan, or program, from a single processing center.

It is another object of the present invention to provide an apparatus and a method which allows an individual to communicate and/or to correspond directly with a benefits provider.

It is yet another object of the present invention to provide an apparatus and a method for providing employee benefits and/or employee benefits information in real-time over a communication network.

It is still another object of the present invention to provide an apparatus and a method for providing employee benefits and/or employee benefits information which stores and/or maintains employee benefits data and/or information by utilizing database management techniques.

It is another object of the present invention to provide an apparatus and a method for providing employee benefits and/or employee benefits information which allows an individual to change, modify, or enhance, benefits in real-time.

It is yet another object of the present invention to provide an apparatus and a method for providing employee benefits and/or employee benefits information which allows an individual to request or order upgrades or downgrades to their existing benefits.

It is still another object of the present invention to provide an apparatus and a method for providing employee benefits and/or employee benefits information which allows employers to pool employee benefits with other employers in order to offer enhanced benefits to their employees.

It is another object of the present invention to provide an apparatus and a method for providing employee benefits and/or employee benefits information which can direct an employee or administrator to a benefits provider or other goods and/or services providers.

It is yet another object of the present invention to provide an apparatus and a method for providing an efficient and enhanced administration of employee benefits, benefits plans and/or benefits programs.

It is still another object of the present invention to provide an apparatus and a method for providing employee benefits and/or employee benefits information which provides for the reduction of employer benefits administration activities and efforts and which provides for the outsourcing of certain employee benefits administrative functions.

It is another object of the present invention to provide an apparatus and a method which allows benefit providers to communicate with the employee or administrator.

It is yet another object of the present invention to provide an apparatus and a method which allows benefit providers to communicate information, including new benefits, enhancements to benefits, or special benefit programs, to employees or administrators.

It is still another object of the present invention to provide an apparatus and a method which provides benefit providers with the ability to offer or sell their respective benefits, services, policies and/or goods, to the employees or administrators.

It is still another object of the present invention to provide an apparatus and a method for providing employee benefits and/or employee benefits information which will provide employees with greater independence in selecting and maintaining employee benefits regardless of their employer and/or employment status.

It is yet another object of the present invention to provide an apparatus and a method for providing employee benefits and/or employee benefits information which provides for the portability of some or all of an employee's benefits, which can be independent of employer and/or employment status.

It is still another object of the present invention to provide a method and an apparatus for providing notification to interested parties of an employee's action to upgrade or change any of the benefits described herein.

It is yet another object of the present invention to provide an apparatus and a method which can provide employee benefits and/or employee benefits information which is independent of an employment relationship.

It is still another object of the present invention to provide an apparatus and a method for providing employee benefits and/or employee benefits information for providing individualized employee benefits which can be portable and which can be independent of an employment relationship and/or which can be taken employment relationship to employment relationship and/or from job to job.

It is another object of the present invention to provide an apparatus and a method for providing employee benefits and/or employee benefit information which can utilize intelligent agents in order to perform any of the herein-described information retrieval, information processing, communication, and/or other tasks for providing employee benefits and/or employee benefits information.

It is still another object of the present invention to provide an apparatus and a method for providing employee benefits and/or employee benefits information for any number of, or for a plurality of, employers or employees.

It is yet another object of the present invention to provide an apparatus and a method for providing employee benefits and/or employee benefits information which can be utilized to provide a clearinghouse for the buying and selling of employee benefits.

It is another object of the present invention to provide an apparatus and a method for providing employee benefits and/or employee benefits information which provides notification of changes and/or modifications to employee benefits.

It is still another object of the present invention to provide an apparatus and a method for providing employee benefits and/or employee benefits information which provides notification of requests for, and/or offerings of, employee benefits.

It is yet another object of the present invention to provide an apparatus and a method for providing employee benefits and/or employee benefits information which provides for the management and/or administration of financial accounts for any of the respective parties utilizing the apparatus and method of the present invention.

It is another object of the present invention to provide an apparatus and a method for providing employee benefits and/or employee benefits information which provides for the effectuation and/or executed of financial transactions for, and/or on behalf of, any of the parties which utilize the present invention.

It is another object of the present invention to provide an apparatus and a method for providing employee benefits and/or employee benefits information which provides notification of financial transactions which occur on, and/or in conjunction with, financial accounts.

It is still another object of the present invention to provide an apparatus and a method for providing employee benefits and/or employee benefits information which provides notification of benefits transactions and/or transactions involving benefits and/or benefits accounts.

It is yet another object of the present invention to provide an apparatus and a method for providing employee benefits and/or employee benefits information which provides for the authentication of, and/or for electronic and/or digital signatures, which can be utilized in conjunction with any and/or all of the various forms, transmissions, and/or communications, which are described herein as being utilized for providing communication between any of the parties described herein.

Other objects and advantages of the present invention will be apparent to those individuals skilled in the art upon a review of the Description of the Preferred Embodiments taken in conjunction with the Drawings which follow.

BRIEF DESCRIPTION OF THE DRAWINGS

In the Drawings:

FIG. 4 illustrates the communication device which is utilized in the apparatus of FIG. 1, in block diagram form.

DESCRIPTION OF THE PREFERRED EMBODIMENT

Figure 1:
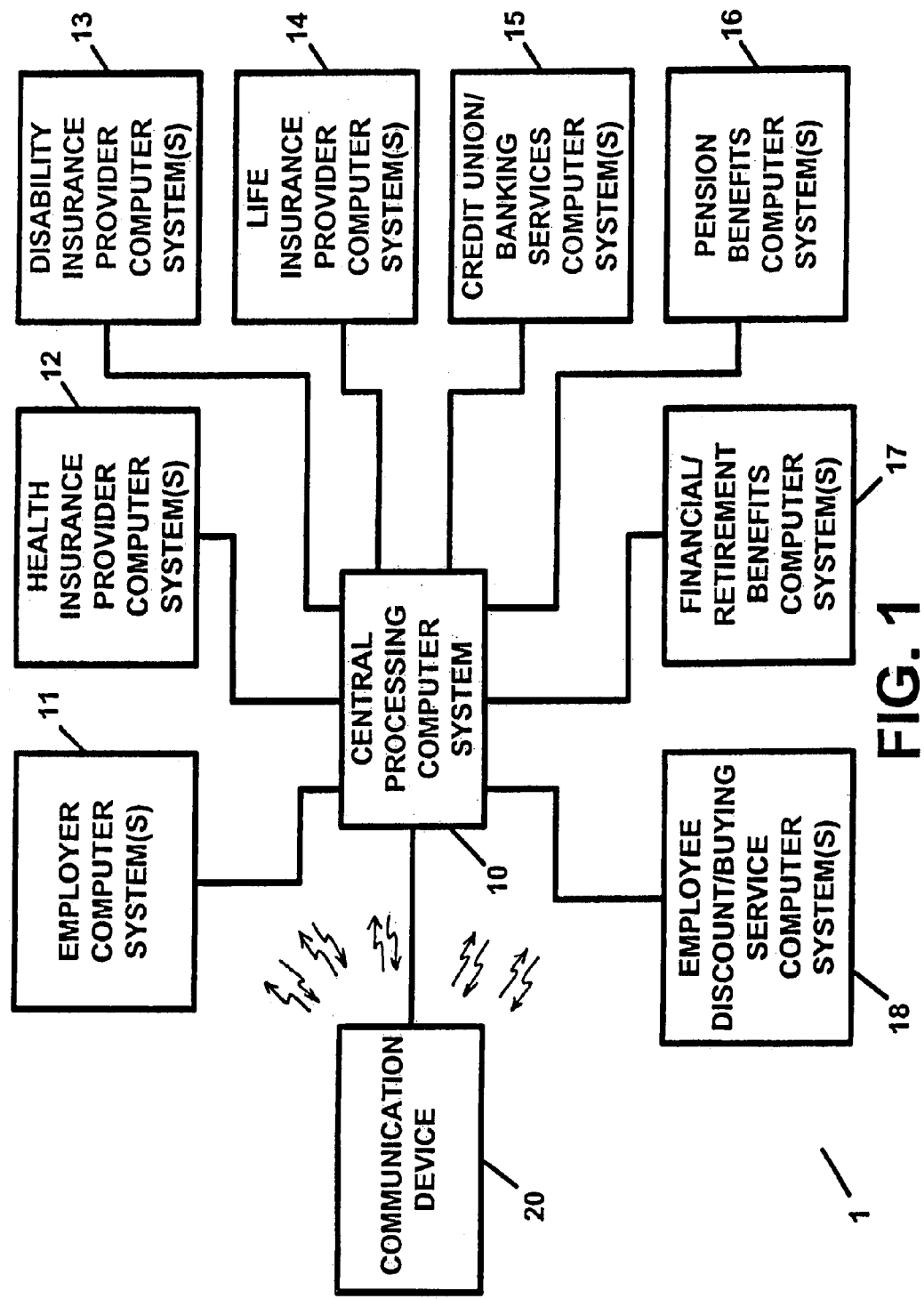
FIG. 1 illustrates the apparatus of the present invention, in block diagram form.

The present invention provides an apparatus and a method for providing employee benefits and/or employee benefits information and/or services. The present invention also provides an apparatus and a method which can be utilized in a network environment. The present invention also provides an apparatus and a method for allowing an employee participant in a benefit plan or program to communicate with his or her employer and/or with any one or more of the benefits providers, described herein, which are associated with his or her benefits package, plan, or program.

The present invention also provides for the access to, and for the administration of, employee benefits and/or employee benefits plans or programs and/or information related thereto. The employee benefits and/or employee benefits plans, programs and/or information include employee wage, salary and payroll information and status, vacation time, sick time and personal time information and status, employee savings plans and programs, employee pension benefits or programs and status of same, employee retirement plans, individual retirement accounts, 401K plans and programs, self-employed retirement plans or programs, or similar retirement plans or programs, employee credit union accounts, plans or programs, employee savings and employee loan plans or programs, health insurance plans or programs, life insurance plans or programs, disability insurance plans or programs, and various employee discount plans and/or buying service plans and/or programs.

Applicant hereby incorporates by reference herein the subject matter of U.S. Provisional Patent Application Ser. No. 60/099,653 which teaches an apparatus and method for providing employee benefits and/or employee benefits information. Applicant also hereby incorporates by reference herein the subject matter of U.S. Provisional Patent Application Ser. No. 60/100,651 which teaches an apparatus and method for providing employee benefits and/or employee benefits information.

The apparatus and method of the present invention, in any and/or all of the embodiments described herein, can be utilized so as to manage, administer, process information regarding, and/or provide any type of employee benefits, benefits services and/or benefits information.

The apparatus and method of the present invention, in any and/or all of the embodiments described herein, can also be utilized to perform any type of human resource functions as well as to process information regarding any type of human resource function. Applicant hereby incorporates by reference herein the subject matter of *The Handbook of Employee Benefits*, Fourth Edition, Jerry S. Rosenbloom, McGraw-Hill, 1996, which describes a wide range of employee benefits and/or human resource functions which can also be managed, administered and/or processed, by the apparatus and method of the present invention.

In the preferred embodiment, the information is provided to an employee, or administrator, or other authorized individual by accessing a central processing computer system, which services the particular employer/employee benefits plan or program, via a communication device such as personal computer or other suitable communication device. The information is stored in a database or in a collection of databases which can be resident on the central processing computer system or on any of the respective benefits providers computer systems.

The information from each benefits providers can be updated in real-time via dynamically linked database techniques. The data and/or information for the comprehensive employee benefits plan or program, in the preferred embodiment, are stored and linked in a relational database scheme.

Applicant hereby incorporates by reference herein the subject matter of U.S. Pat. No. 4,648,037 which discloses a method and apparatus for benefit and financial communication.

The terms "benefits" and/or "employee benefits", as the terms are utilized herein, refer to any and/or all of the employee benefits, benefits, and/or other benefits, offered by employers, employing entities, and/or by any of the various benefits providers and/or providers which are described herein, and/or to any benefits which are, or which may be, offered as a benefit, as an employee benefit, as compensation, and/or as part of a compensation package, pursuant to an employment relationship, an independent contractor relationship, and/or any other type of relationship.

The benefits and/or employee benefits can also include any benefit or compensation. The benefits and/or employee benefits can also include any benefits described in *The Handbook of Employee Benefits*, Fourth Edition, Jerry S. Rosenbloom, McGraw-Hill, 1996, the subject matter of which is incorporated by reference herein.

FIG. 1 illustrates the apparatus of the present invention which is designated generally by the reference numeral 1, in block diagram form. In FIG. 1, the apparatus includes a central processing computer system 10 or server computer which will receive and store the pertinent information regarding the employee benefits, plans, or programs, from each of the pertinent benefits providers and information sources described herein.

The apparatus of FIG. 1 also includes an employer computer 11, which is linked with the central processing computer system 10. Employer information regarding each individual employee which can include job title, length of service, salary, withholding taxes, vacation time, sick time and personal time, along with any other personnel information pertinent to the employee and/or to the employee's benefits package, is provided by the employer computer system 11 to the central processing computer system 10. The employer computer system 11 may include any number of computers for facilitating the provision of any and all of the information described herein to the central processing computer system 10.

The employer information will also include information regarding the various benefits providers, such as, for example, health insurance providers, disability insurance providers, life insurance providers, credit unions and banking services providers, pension benefits providers, retirement benefits providers, and various employee discount and buying service providers.

The apparatus 1 also includes a health insurance computer system 12 which is also linked to the central processing computer system 10. The health insurance computer system 12 may include at least one computer system which corresponds to each of the medical insurance provider or providers, dental insurance provider or providers, health maintenance organizations (HMOs), and major medical providers, etc., associated with the benefits plan or program.

Each of the various health insurance providers can provide employee benefit information, including benefits available, instructions for obtaining and/or claiming benefits, health-care participants, health care providers, coverages under the plan, co-payments and/or deductibles, claims information, status of claims, and other pertinent information regarding the employee's health benefits.

The apparatus 1 also includes a disability insurance computer system 13 which is also linked to the central processing computer system 10. The disability insurance computer system 13 may include at least one computer system corresponding to each of a disability insurance providers which may include the short-term disability insurance provider or providers, the long-term disability insurance provider or providers, and any other disability insurance provider or providers which may be associated with the employee benefits plan or program.

Each of the various disability insurance providers can provide employee disability benefits information, including benefits available, instructions for obtaining and/or claiming benefits, coverages under the plan, co-payments and/or deductibles, claims information, status of claims, and other pertinent information regarding the employees disability benefits.

The apparatus 1 also includes a life insurance computer system 14 which is also linked to the central processing computer system 10. The life insurance computer system 14 may include at least one computer system corresponding to each of the life insurance providers which may be associated with the employee benefits plan or program.

Each of the various life insurance providers can provide employee life insurance benefits information, including benefits available, instructions for obtaining and/or claiming benefits, coverages under the plan, co-payments and/or deductibles, claims information, status of claims, and other pertinent information regarding the employee's life insurance benefits.

The apparatus 1 also includes a credit union or banking services computer system 15 which is also linked to the central processing computer system 10. The credit union or banking computer system 15 may include at least one computer system corresponding to each of the credit union or banking institutions which may be associated with the employee benefits plan or program.

Each of the credit union or banking services providers can provide information concerning the benefits and/or services available, instructions for obtaining and/or claiming benefits, as well obtaining information regarding the employee's savings account(s), loan information, mortgages, including benefits available to the employee such as savings interest rates, loan and mortgage rates available to the employee, as well as any other financial information concerning the employee's benefits which are provided and/or offered by the respective credit union(s) and/or banking services providers under the employee benefits plan or program.

The apparatus 1 also includes a pension benefits computer system 16 which is also linked to the central processing computer system 10. The pension benefits computer system 16 may include at least one computer system corresponding to each of the pension benefits provider(s) which may be associated with the employee benefits plan or program. Each of the pension benefits providers can provide information concerning the services provided, instructions for obtaining benefits, as well as information regarding the employee's pension account(s), loan information and/or pension benefits and/or services which are available to the employee.

The pension benefits computer system 16 can also provide information regarding pension benefits available, vested and unvested benefits, availability of benefits and financial advice, planning and forecasting services and/or information, status of pending claims and any other information concerning the employee's pension benefits under the employee's pension benefits plan or program.

The apparatus 1 also includes a financial/retirement benefits computer system 17 which is also linked to the central processing computer system 10. The financial/retirement benefits computer system 17 may include at least one computer system corresponding to each financial institution(s) which are associated with the employee's retirement benefits plan or program and/or which manages the employee's retirement account(s), 401K account, individual retirement account (IRA), employee profit sharing account, employee stock ownership or purchasing account, stock option account, as well as any other pertinent financial account which may be associated with, or related to, the employee's retirement benefits plan or program.

Each of the financial providers can provide information concerning the employee's retirement benefits, retirement savings, savings accounts, loan information, stock accounts, mutual fund accounts, stock option accounts including information which is available to the employee such as savings interest rates, loan and mortgage rates and other products and/or services available to the employee.

Other information which can be provided can include instructions for claiming retirement benefits, information regarding the various benefits and retirement investment vehicles, instructions for making account deposits and withdrawals, deposit and withdrawal procedures. Other information which can be provided includes account balances, vested and unvested amounts, availability of benefits and/or funds, as well as financial advise, planning an/or forecasting information. The retirement benefits computer system 17 can also provide information concerning the employee's retirement benefits offered by respective benefits providers under the employee's benefits plan or program.

The apparatus 1 also includes an employee discount and/or buying service computer system(s) 18 which is also linked to the central processing computer system 10.

The employee discount and/or buying service computer system(s) 18 may include at least one computer system which corresponds to each of the providers of employee discounts and/or buying services which are provided under the employee benefits plan or program to the respective employees. The employee discount and/or buying service providers can include any goods and/or service provider(s) and/or buying services, discount clubs, etc., which provide discounts and/or buying services to employees under the benefits plan or program.

Each of the employee discount and/or buying service providers can provide information concerning their respective employee discount programs and/or buying services, including the goods and/or services which they provide, which are available to the employees, instructions and/or information for ordering goods and/or services and/or for making purchases, placing orders, obtaining customer service, as well as checking order status and obtaining any other pertinent information associated with the benefits plan or program.

The apparatus 1 also includes a communication device 20 which is also linked to the central processing computer system 10. The communication device 20 can be utilized by the employees, as well as by administrators, in order to access the central processing computer system 10, as well as any one or more of the provider computer systems 11-18, in order to access and/or obtain any of the benefits and/or benefits information which are provided by the apparatus 1 of the present invention as described herein.

The communication device 20, in the preferred embodiment, is a personal computer, or a desktop computer, or any other appropriate communication device, which may be located at any appropriate location, such as the employee's workplace, home, or at a public or semi-public kiosk, which may utilized by the employee or administrator, in order to access employee benefits and/or employee benefits information. As described herein the communication device 20 can access the central processing computer system 10, and any of the provider computer systems 11-18, in order obtain employee benefits and/or employee benefits information.

The employee or administrator can also provide data and/or information to the central processing computer system 10 and to any of the provider computer systems 11-18, via the communication device 20 as will be described in more detail herein.

The communication device 20 may be any one of a personal computer, a desktop computer, a laptop computer, a personal digital assistant, a telephone, a television, an interactive television, a handheld computer, a palmtop computer, or any other suitably equipped personal communication device.

In the preferred embodiment, the present invention is utilized on, or over, the Internet and/or the World Wide Web. In this regard, the various apparatus components, including the computers system 10-18 and the communication device 20, are linked via the Internet and/or the World Wide Web and the corresponding networks and/or systems. Each of the computers systems 10-18 and the communication device 20 will therefore transmit data and/or information using TCP/IP, as well as all other Internet and/or World Wide Web, protocols. The present invention may also be utilized on, or over, any other communication network or system.

The communications networks and/or systems on, or over, which the present invention may be utilized, include any one or combination of telecommunication networks or systems, satellite communication networks or systems, radio communication networks or systems, digital communication networks or systems, digital satellite communication networks or systems, personal communications services networks or systems, cable television networks or systems, broadband communication networks or systems, low earth orbiting satellite (LEOs) networks or systems, as well as in or on any internets and/or intranets, the Internet, the World Wide Web, and any other suitable communication network or system.

Figure 2:
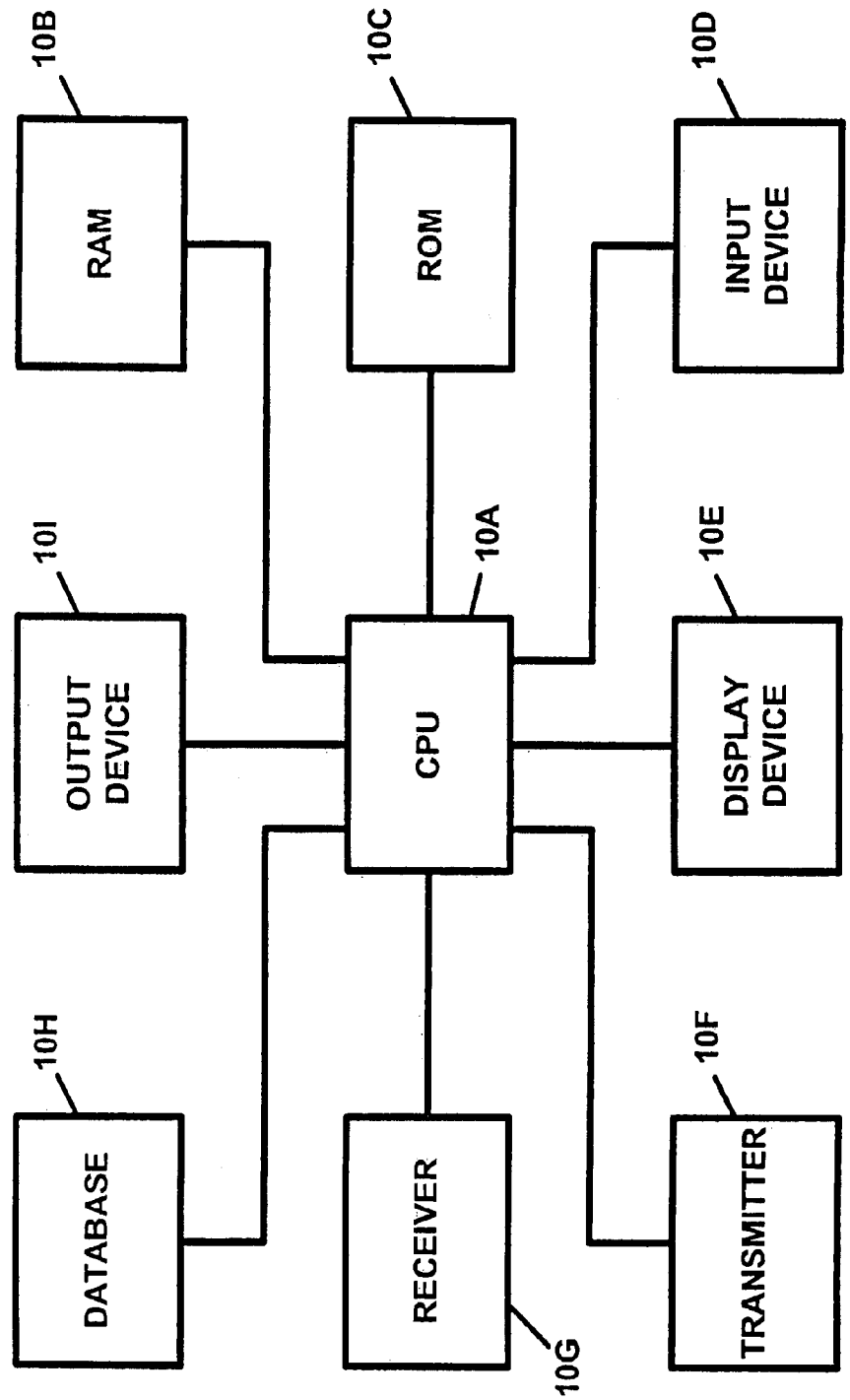
FIG. 2 illustrates the central processing computer system which is utilized in the apparatus of FIG. 1, in block diagram form.

FIG. 2 illustrates the central processing computer system 10, in block diagram form. The central processing computer system 10, in the preferred embodiment, is a network computer system which is utilized as a server computer such as an Internet server computer and/or a Web server computer. In the preferred embodiment, the central processing computer system 10 includes a central processing unit or CPU 10A, which in the preferred embodiment, is a microprocessor. The CPU 10A may also be a microcomputer, a minicomputer, a macro-computer, and/or a mainframe computer, depending upon the application.

The central processing computer system 10 also includes a random access memory device(s) 10B (RAM) and a read only memory device(s) 10C (ROM), which are connected to the CPU 10A, a user input device 10D, which is a keypad and/or any other suitable input device for inputting data into the central processing computer system 10 and which is also connected to the CPU 10A. The central processing computer system 10 also includes a display device 10E for displaying information and/or data to a user or operator.

The central processing computer system 10 also includes a transmitter(s) 10F for transmitting signals and/or data to any one or more of the communication devices 20 which may be utilized, the employer computer system(s) 11, the health insurance computer system(s) 12, the disability insurance computer system(s) 13, the life insurance computer system(s) 14, the credit union or banking services computer system(s) 15, the pension benefits computer system(s) 16, the financial/retirement benefits computer system(s) 17, and the employee discount and/or buying service computer system(s) 18.

The central processing computer system 10 also includes a receiver 10G for receiving signals and/or data from any one or more of the communication device(s) 20, the employer computer system(s) 11, the health insurance computer system(s) 12, the disability insurance computer system(s) 13, the life insurance computer system(s) 14, the credit union or banking services computer system(s) 15, the pension benefits computer system(s) 16, the financial/retirement benefits computer system(s) 17, and the employee discount and/or buying service computer system(s) 18.

As described herein, the central processing computer system 10, the communication device(s) 20, the employer computer system(s) 11, the health insurance computer system(s) 12, the disability insurance computer system(s) 13, the life insurance computer system(s) 14, the credit union or banking services computer system(s) 15, the pension benefits computer system(s) 16, the financial/retirement benefits computer system(s) 17, and the employee discount and/or buying service computer system(s) 18 are linked via a communication network or system.

In another preferred embodiment, the central processing computer system 10 and the individual provider computer system 11-18 can be integrated into a single computer system. In yet another preferred embodiment, the communication device 20 may be integrated with any one or more of the central processing computer system 10 and/or with any of the provider computers 11-18. In this manner, the communication device 20, in a preferred embodiment, can be a terminal device for any one or more of the central processing computer system 10 and/or any one or more of the provider computer systems 11-18.

The central processing computer system 10 also includes a database(s) 10H which contains data and/or information pertaining to some or all of the employee benefits plans and/or programs, and/or portions thereof, which are described herein. The database 10H may also include a collection of databases for storing pertinent data and/or information.

The database 10H, in the preferred embodiment, is a database which may include individual databases or collections of databases, with each being designated to store data and/or information for each of the various employee benefits and related benefits which are available to each of the employees covered thereby. In the preferred embodiment, the database 10H and/or any other database or collection of databases utilized by the present invention, also contains data and/or information regarding each employee which is covered under an employee benefits plan or program which is serviced by the apparatus 1 of the present invention.

Employee benefits data and/or information, for each of the benefits provided, including employer benefits, health insurance benefits, disability insurance benefits, life insurance benefits, credit union or banking services benefits, pension benefits, financial/retirement benefits, and employee discount or buying service benefits, in the preferred embodiment, are stored in the database 10H, or in the collection of databases.

The data and/or information in the database 10H, or in the collection of databases, can be linked via relational database techniques and/or via any appropriate database management techniques. The data and/or information, in the preferred embodiment, are updated via inputs from the respective providers benefits computers 11-18 via the communication network. The database 10H, or collection of databases, or any databases utilized in the present invention, can be updated by each of the respective benefits providers, in real-time, and/or via dynamically linked database management techniques.

Figure 3:
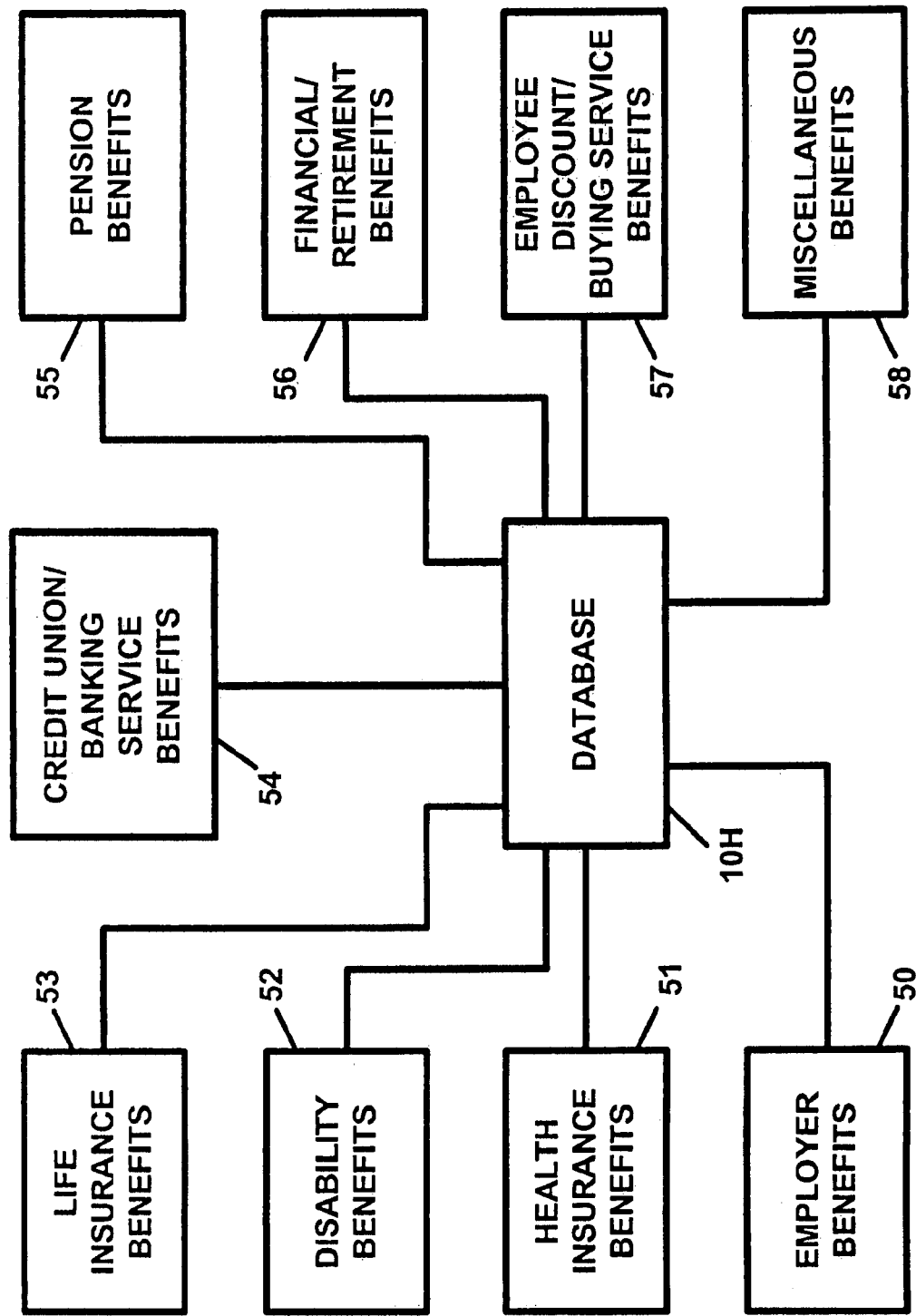
FIG. 3 illustrates the configuration of the database which is utilized in the central processing computer system of FIG. 2.

FIG. 3 illustrates the database configuration of the database 10H. In FIG. 3, the database 10H includes databases for each the employer benefits 50, the health insurance benefits 51, the disability benefits 52, the life insurance benefits 53, the credit union or banking services benefits 54, the pension benefits 55, the financial/retirement benefits 56, and the employee discount or buying service benefits 57, as well as any other miscellaneous employee benefits 58.

With reference once again to FIG. 2, the central processing computer system 10 also includes an output device 10I such as a printer, a modem, a fax/modem or other output device for providing data and/or information to the operator or user of the central processing computer system 10 or to a third party or third party entity.

In the preferred embodiment, each of the employer computer system(s) 11, the health insurance computer system(s) 12, the disability insurance computer system(s) 13, the life insurance computer system(s) 14, the credit union or banking services computer system(s) 15, the pension benefits computer system(s) 16, the financial/retirement benefits computer system(s) 17, and the employee discount or buying service computer system(s) 18, include the same, similar or analogous components and/or peripheral devices as the central processing computer system 10. In this manner, each of the provider computer systems 11-18 can be network computers, or server computers, which may be the same as, or similar to the central processing computer system, which, in the preferred embodiment, is also a network computer, or server computer.

The database 10H, or collection of databases which form the database 10H, as well as any other database described herein, can be implemented by utilizing database software and/or spreadsheet software, such as, for example, Microsoft™ Access™ and/or Microsoft™ Excel™ or any other suitable database or spreadsheet software programs and/or systems.

The data and/or information which is provided by the various benefits providers can be downloaded to, and/or be resident upon the central processing computer system 10, or a portion of the data and/or information, may be downloaded to, and be resident in the central processing computer system 10 with other and/or additional data and/or information being stored at the respective provider computers systems 11-18, as desired.

The data and/or information which is utilized in, and/or provided by, the present invention can be linked via any suitable data linking techniques such as, for example, dynamically linked lists (DLLs), linked lists, and object links embedded (OLE's) as well as any other database management techniques which are known to those skilled in the art.

FIG. 4 illustrates the communication device 20, in block diagram form. The communication device 20 is linked to the central processing computer system 10 over the communication network in order to facilitate the accessing of employee benefits and/or employee benefits information from the central processing computer system 10. The communication device 20 can also be described as being a communication device.

The communication device 20 is also linked to each of the employer computer system(s) 11, the health insurance computer system(s) 12, the disability insurance computer system(s) 13, the life insurance computer system(s) 14, the credit union or banking services computer system(s) 15, the pension benefits computer system(s) 16, the financial/retirement benefits computer system(s) 17, and the employee discount or buying service computer system(s) 18, via the central processing computer system 10 by utilizing appropriate links to these respective provider computer systems 11-18.

The communication device 20 may also be directly linked to each of the respective provider computer systems 11-18. The computer systems 11-18 may hereinafter be referred to as the "providers computer systems 11-18" or "provider computers 11-18".

The apparatus 1 of the present invention may be utilized on, or over, any communications network or system. In the preferred embodiment, the apparatus 1 is utilized on, or over, the Internet and/or the World Wide Web.

In the preferred embodiment, wherein the apparatus 1 is utilized over the Internet and/or the World Wide Web, hyperlinks and/or other data and/or information links and/or linking methods can be utilized in order to provide the mechanism by which an employee can access the central processing computer system 10 and any of the provider computer systems 11-18 and/or to any of the data and/or information contained therein or resident thereon. In this manner, the employee or administrator can gain access to, or obtain, any of the employee benefits and/or benefits information which is provided and/or made accessible by the present invention.

The central processing computer system 10, and any of the providers computer systems 11-18 described herein, in the preferred embodiment, are server computers. The communication device 20, in the preferred embodiment, is a communication device.

With reference to FIG. 4, the communication device 20 includes a central processing unit (CPU) 20A which, in the preferred embodiment, is a microprocessor. The CPU 20A may also be a microcomputer, a minicomputer, a macrocomputer, and/or a mainframe computer, depending upon the application.

The communication device 20 also includes a read only memory (ROM) device(s) 20B and random access memory (RAM) device(s) 20C which are also connected to the CPU 20A. The communication device 20 also includes a user input device(s) 20D which includes any one or more of a keyboard, a scanner, a user pointing device, such as, for example, a mouse, a touch pad, and/or an audio input device and/or a video input device, etc., if desired, which input device(s) are also connected to the CPU 20A.

The communication device 20 also includes a display device 20E, such as a display monitor, which is also connected to the CPU 20A, and an output device 20F, such as a printer, a fax/modem, etc., which output device is also connected to the CPU 20A. Both the display device 20E and the output device 20F provide information to the employee or administrator regarding the employee benefits and/or information related thereto. All benefits and/or benefits information described herein can be displayed on the display device 20E and output via the output device 20F.

The communication device 20 also includes a database(s) 20G, wherein various benefits plan or program data and/or information can be stored and maintained for use as needed and/or when necessary. The communication device 20 also includes a transmitter 20H for transmitting data and/or information to any one or more of the central processing computer system 10 and to any of the employer computer system(s) 11, the health insurance computer system(s) 12, the disability insurance computer system(s) 13, the life insurance computer system(s) 14, the credit union or banking services computer system(s) 15, the pension benefits computer system(s) 16, the financial/retirement benefits computer system(s) 17, and the employee discount or buying service computer system(s) 18.

The communication device 20I also includes a receiver 20I for receiving data and/or information from any one of the central processing computer system 10 and from any one or more of the employer computer system(s) 11, the health insurance computer system(s) 12, the disability insurance computer system(s) 13, the life insurance computer system(s) 14, the credit union or banking services computer system(s) 15, the pension benefits computer system(s) 16, the financial/retirement benefits computer system(s) 17, and the employee discount or buying service computer system(s) 18.

The employee, or administrator, may obtain employee benefits and/or employee benefits information by utilizing the present invention. The employee may also obtain information regarding his or her employment status and benefits which are provided to the employee. The employee may obtain information, instructions and/or explanations regarding benefits, instructions for obtaining and claiming benefits, make benefit elections or changes to benefits, change investments in savings, pension and retirement accounts, apply for additional benefits, and file claims for health insurance, disability, or life insurance benefits.

The employee or administrator, can also make purchases and/or place orders in connection with any of the employee discount programs and/or buying services provided as part of the employee benefits plan or program. The present invention allows an employee to obtain, access, and/or take advantage of, any and all employee benefits and/or employee benefits information which are made available under the employee benefits plan or program.

The apparatus of the present invention provides an apparatus and a method for allowing the employee, or administration to access and/or obtain any employee benefits, employee services and/or information related thereto at any time and from any location over a communication network.

In the preferred embodiment, the employee benefits data and/or information is provided to an employee or other authorized individual by accessing the central processing computer system 10, which services the particular employee benefits plan or program, via the communication device 20. All of the benefits and/or related information is stored in a database or a collection of databases which may be resident on the central processing computer system and/or which may be resident, in whole or in part, on any of the providers computer systems 11-18.

All pertinent benefits information can be obtained and updated from each benefits provider, in real-time over the communications network, via dynamically linked lists and other database management techniques. In this manner, the data and/or information for up-to-date apparatus processing can be obtained and be made readily available to any and all of the appropriate computer systems 10-18 of the apparatus 1.

The present invention can be utilized, in a preferred embodiment, in the following manner. The employee or administrator can access the central processing computer system 10 via the communication device 20. The apparatus 1, in the preferred embodiment, provides data and/or information via a menu-driven and/or via a graphical user interface scheme or environment. The employee will typically be asked to provide a user name and a password in order to obtain access to the central processing computer system 20. The operation of the central processing computer system 10, in the preferred embodiment, is menu-driven.

The employee, or administrator, can be provided with a home page and/or home page menu, associated with the employee's benefits plan or program, on the display device 20E of the communication device 20. The home page and/or home page menu will display a menu of items from which the employee may make a selection. The menu list will include the information regarding the various benefits and/or benefits categories of employee benefits and/or employee benefits information which are available to the employee or administrator.

The home page menu, in the preferred embodiment, will include personnel information, health insurance information, disability insurance information, life insurance information, credit union or banking services information, pension benefits information, retirement account information, employee discount or buying service(s) information, as well as any other categories of information which may be related to the employer's benefits plan or program.

Each of the above and/or additional benefits categories can be linked to the data and/or information for the individual employee and may be accessed via the home page menu. Further, as described herein, links may be provided for obtaining any data and/or information which is provided by the apparatus 1 or from other related data and/or information sources which may be pertinent to the employee benefits plan or program.

The employee, or administrator, can select personnel information which will link the employee to a personnel page which will provide personnel information which can include the employee's name, address, social security number, date of birth, date of hire, payroll information, salary information, payroll withholdings and deductions information, tax exemption status, company stock account, stock options account, and/or equity interest account, if any, which the employee may hold in the company.

Payroll, withholding and deduction information can include the number of dependents, federal withholding taxes, state withholding taxes, local withholding taxes, social security taxes, disability taxes, disability withholding taxes, retirement deductions, pension deductions, IRA deductions, 401K deductions, SEP deductions, savings deductions, savings bond deductions, stock purchase plan deductions, employer held savings accounts, credit union deductions, etc.

The personnel information can also include tuition reimbursement programs, educational assistance programs, child care or day care programs. Personnel information can also include in-house training courses, training and educational courses set up outside the company, as well as schedules, course descriptions and registration information. The employee can register for classes for any of the above courses and/or programs on-line and may do so via e-mail or via subscription forms which can be filed electronically via the communication device 20.

The employee can also request tuition reimbursement on-line. The employee can also fill out and file expense accounts via the personnel page.

The personnel page can also contain other information such as company announcements, company calendars and/or schedules, personnel directories, and/or in-house job postings, etc. The employee can communicate with other employers, apply for in-house job openings, etc, on-line via the personnel page.

The information provided on the personnel page may be provided with links to separate pages which provide additional information on the topic selected as well as more detailed data. For example, if the employee desires to obtain information of on his or her pension benefits, the employee may elect to obtain more information by selecting pension benefits on the display device 20E of the communication device 20 and, thereafter, a pension benefits screen will provide information explaining the benefits plan and the employees vested and/or non-vested interests. The plan would also provide information on the vesting period(s)for the pension plan. In a similar manner, the present invention provides information for each of the benefits provided on, or via, the personnel page.

The personnel page also includes information regarding the employee's health insurance benefits and provider(s), disability insurance benefits and provider(s), life insurance benefits and provider(s), pension benefits and provider(s), retirement benefits and provider(s), credit union or banking services benefits and provider(s), and employee discount and/or buying service benefits and provider(s). Links to the above benefits pages can be provided on, or via the personnel page and/or the home page.

The employee can also obtain any employee benefits and/or employee benefits information, submit changes to benefits, submit benefits claims, register and/or subscribe to any of the employee benefits described herein, and/or make inquiries and/or status inquiries regarding employee benefits and/or employee benefits claims.

The employee can also transmit messages to the employer via e-mail transmission, facsimile transmission, electronic form submission or transmission, and/or by any other communication means, in order to allow the employee make changes to any of his or her employee benefits. For example, the employee may change the amount of payroll deductions and/or make other changes to other personnel information which corresponds to the employee. The employee may also effect any changes and/or modifications to any of the data and/or information described herein, on-line via the communication device 20.

The employee or administrator can also access health insurance benefits and/or information related thereto from the home page, such as by accessing a health insurance benefits page, which will provide the employee or the administrator with a listing of all of the health insurance benefits available to the employee in his or her benefits package as well as the health insurance benefits provider(s) associated therewith. The various benefits can include health maintenance organization (HMO) information, medical insurance information, major medical insurance information, dental insurance information, mental health insurance information, prescription eye care insurance information, and any other available health care benefits and information.

Each coverage type and/or provider can have a separate page associated therewith. The employee may select any one of the benefits types and/or the respective providers and be linked to a separate page dedicated to the particular benefits and/or provider(s). The page which is dedicated to each provider or coverage type will provide a detailed explanation of the coverage and/or benefits provided, applicable deductibles or co-payments under the plan, instruction for obtaining benefits and/or directories and/or listings of providers, etc.

The employee can select a primary care provider, if applicable, for each of the various benefits provided. The employee can also change primary care provider(s), request referral authorizations for specialists. The employee can also submit claims on-line and check the status of claims which are pending.

The employee may also communicate directly with the health care benefits provider by submitting communications via e-mail transmissions, facsimile transmission, electronic form submissions or transmissions, and/or by any other communication means. The employee can also purchase upgraded benefits and/or change coverages, directly from the benefits provider, on-line via the communication device 20, in order to receive enhanced and/or upgraded benefits. For example, the employee can agree to purchase enhanced benefits, which may provide for greater coverage's, additional types of coverage's, decreased deductibles or co-payments, increased dependents on the policy, etc, simply by ordering same on-line via the communication device 20.

The employee, in any of the embodiments and for any benefits described herein, can provide credit card information, debit card information, bank account withdrawal information, and/or payroll deduction information and/or authorization information on-line in order to pay for benefit upgrades and/or changes. This feature will allow an employee to take advantage of coverage already provided by the employer and obtain enhancements and/or upgrades for this coverage from the same provider of the basic benefits as well as receive said enhancements and/or upgrades at a savings and/or without having to obtain same from a different benefits provider. The employer can be notified regarding any transactions described herein between the employee and the respective health care benefits provider.

Each of the above or additional benefits and/or information related thereto can be linked to the via the home page menu. Further, as described herein, links may be provided for any data and/or information provided by the apparatus 1 which may pertinent to the employee benefits plan or program.

The employee can also access disability insurance benefits and information related thereto, from the home page, which will provide the employee with a listing of all of the disability insurance benefits (i.e. short-term disability, long-term disability, etc.) which are available to the employee in his or her benefits package, as well as the disability insurance benefits provider(s) associated with these benefits. The various benefits can include short-term disability benefits, long-term disability benefits, as well as any other disability benefits which may be available.

The employee may select any one of the benefits types, and/or the associated disability benefits providers, and be linked to a separate page devoted to disability insurance benefits and/or to the corresponding provider(s). A page can be dedicated to each benefits type and/or to each provider. The page can provide a detailed explanation of the benefits provided, instructions and/or information for obtaining and/or claiming benefits, information regarding filing a disability insurance claim, applicable deductibles and/or co-payments under the plan, directories and/or listings of individuals, doctors and/or other individuals and/or entities which have to be notified and/or contacted in order to file a disability insurance claim.

The employee can select a disability care provider, if applicable, for each of the various benefits provided. The employee can also change provider(s) and/or request referral authorizations for specialists. The employee can also submit disability insurance claims on-line, via the communication device 20, and check the status of pending claims.

The employee may also communicate directly with the disability insurance provider by submitting communications via e-mail transmission, facsimile transmission, electronic form submission or transmission, and/or by any other communication means. The employee can also purchase upgraded disability benefits directly from the provider, on-line, via the communication device 20, in order to obtain enhanced and/or upgraded disability benefits.

For example, the employee can agree to purchase enhanced benefits, which may provide for greater coverage's, additional types of coverage's, decreased deductibles or co-payments, increased dependents on the policy, etc., simply by ordering same on line, via the communication device. The employee may provide credit card information, debit card information, bank account withdrawal information, and/or payroll deduction information and/or authorization information on-line in order to pay for the changes and/or enhancements to his or her disability benefits.

This feature will allow an employee to take advantage of disability insurance benefits and the relationship with the respective benefits provider, already provided by the employer, in order to obtain enhancements and/or upgrades for disability insurance benefits from the same provider. The employee may also obtain enhanced benefits at a savings and without having to obtain same from a different benefits provider. The employer can be notified regarding any transactions described herein between the employee and the respective disability benefits provider.

The employee can also access life insurance benefits and/or information related thereto from the home page which will provide the employee with a listing of all of the life insurance benefits which are available to the employee in his or her benefits package as well as the life insurance provider(s) associated with these benefits. The various benefits can include term life insurance, whole life insurance, as well as any combination thereof and/or other life insurance benefits which may be available and/or be provided.

The employee may select the life insurance benefits and/or life insurance provider(s) and be linked to a separate page devoted to the life insurance benefits and/or providers. A page which can be dedicated to each benefit and/or provider can provide a detailed information and/or an explanation of life insurance benefits provided under the benefits plan or package, coverages and/or benefits provided, information regarding filing a life insurance claim, applicable deductibles or co-payments under the plan, directories and/or listings of individuals, and/or other entities which have to be notified and/or contacted in order to file a life insurance claim.

The employee, an administrator, or an employee's representative, can also submit life insurance claims and check the status of claims which are currently pending, on-line via the communication device 20.

The employee can also communicate directly with the life insurance provider by submitting communications via e-mail transmission, facsimile transmission, electronic form submission or transmission, as well as by any other communication means. The employee may also purchase upgraded benefits directly from the provider or carrier, on-line via the communication device 20, in order to receive enhanced and/or upgraded life insurance benefits.

For example, the employee can agree to purchase enhanced benefits, which may provide for greater coverage's, additional types of coverage's, decreased deductibles or co-payments, increased dependents on the policy, etc, simply by ordering same on-line. The employee may provide credit card information, debit card information, bank account withdrawal information, and/or payroll deduction information and/or authorization information, on-line via the communication device 20, in order to make changes and/or upgrades to his or her life insurance benefits.

In this manner, an employee can take advantage of life insurance benefits and the relationship with the provider, which are already provided by the employer, and obtain enhancements and/or upgrades for his or her life insurance benefits from the same provider. The employee may also obtain benefits enhancements and/or upgrades at a cost savings and without having to obtain same from a different provider. The employer can be notified regarding any transactions described herein between the employee and the respective life insurance provider(s).

The employee can also access employee credit union and/or banking services and/or information related thereto from the home page which will provide the employee with a listing of all of the accounts which the employee holds as well as benefits which are provided by the union and/or banking services provider(s). The employee may access account balances, authorize or terminate payroll deductions into his or her account or accounts, order checks, make payments, stop payments, apply for loans and/or mortgages, purchase certificates of deposits, bonds etc., as well as perform any banking and/or savings activity, on-line and via the communication device 20.

The employee can also obtain financial advice, obtain information regarding benefits offered by the credit union and/or banking services providers, obtain special rate loans offered to employees, apply for mortgages, purchase stocks, bonds, mutual funds, savings bonds, etc., as well as perform other savings and/or financial transactions with the credit union and/or banking services provider(s) which are associated with their accounts and/or with their employer.

The employee can also obtain forecasts for his or her savings account(s) or programs in order to determine future account values and/or financial planning strategies which may be needed to reach certain goals. A credit union and/or banking services page can also include information about company stock purchases made through a company-sponsored plan, as well as saving bond purchasing plans along with portfolio information concerning the employee's account.

The employee can also access pension benefits and/or pension benefits information from the home page which will provide the employee with information about his or her pension benefits, including a description of the pension benefits, vested as well as unvested interests, total account values and balances, lists and dates of employer contributions, lists and dates of employee contributions, if applicable, funds availability information, as well as information regarding investment vehicles and investment options which are available to the employee.

The employee can allocate pension funds among various investment vehicles and/or options. The employee can also change employee contributions on-line so as to increase or decrease his or her contributions to his or her pension plan. The employee can also file claims for pension benefits and determine the status of pending claims.

The employee can also request and obtain financial advice for managing their pension benefits accounts, obtain information regarding their accounts, and/or obtain information on special loan offerings, and investment offerings. The employee can also obtain forecasts for his or her pension accounts in order to determine future account values and/or to obtain financial planning strategies which may be needed to reach certain goals. The pension benefits page can also include information about company stock purchases which can be made through a company-sponsored plan as well as other information regarding pension benefits.

The employee can also access retirement benefits information from the home page which will provide the employee with information about his or her employer sponsored retirement account(s). Information can be obtained from a retirements benefits page. In the case of self-employed individuals, information can be obtained regarding self employed retirement programs and/or accounts. Other retirement accounts such as those not covered by 401K or SEP regulations can also be accessed, if provided.

The employee can obtain information about their retirement accounts, investment options and investment vehicles provided, account values and balances, vested and unvested values, lists and dates of employer contributions, lists and dates of employee contributions, and/or lists and dates of profit sharing contributions, if applicable, as well as information as to how, when and under what circumstances the account monies may be withdrawn and/or borrowed and the interest rates which may apply thereto.

The employee can allocate retirement funds among various investment vehicles and options, on-line via the communication device 20. The employee can also change any employee contributions on-line so as to increase or decrease his or her contributions to a retirement account or accounts.

The employee can also access employee discount and/or buying service benefits and/or information related thereto from the home page. An employee discount and/or buying service benefits page can provide information regarding various employee discounts and/or buying services which are available to the employee from various participating goods and services providers as well as various buying services which participate in the employee benefits plan or program.

The employee can be provided with appropriate links to the various employee discount and/or buying service providers so that the employee or administrator can contact the web pages or home pages of, and/or the various goods and services providers directly. The employee may also place orders on-line with any of these goods and/or services providers as well as register with, or subscribe to, any of these goods and/or services providers. The employee can also check the status of pending orders which have been made or placed via the apparatus.

The employee can also be provided with links to goods and/or services providers so as to enable the employee to contact the goods and/or service providers directly.

The present invention provides an apparatus and a method for providing employee benefits and/or employee benefits information. The present invention also provides for an apparatus and a method for administering employee benefits plans and/or programs. The present invention, by providing centrally maintained and managed benefits and/or benefits information, can also provide for the outsourcing of certain employer benefits administration activities.

Any and all of the benefits and/or benefits information described herein can be accessed via the central processing computer system in a web site environment with thew home page providing access to each page or to pages of information which can correspond with each of the employee benefits described herein. Each of the above or additional benefits and/or information related thereto can be linked to the data and/or information for the individual employee and may be accessed via a home page menu. Further, as described herein, links may be provided for any data and/or information provided by the apparatus 1 to other related data and/or information which may be pertinent to and/or related to the employee benefits plan or program.

The present invention can be utilized to allow employees to custom tailor their benefits packages so as to fit their needs by allowing them to correspond directly with their benefits providers. Employees can also change, modify, upgrade, or downgrade, their benefits as they desire. This ability to allow the employees direct access to their providers can result in more personalized relationships between individual employees and their benefits providers.

The present invention will allow employees to maintain and continue their relationships with their respective benefits providers even after their employment relationship, which brought the employee to the provider together, may cease to exist. In this manner, the present invention provides employees with the opportunity to continue certain or all of their employment benefits in spite of changes in employment, changes in employer and/or changes in employment status.

In this manner, the relationships between employees and the respective benefits providers will facilitate the creation of individual benefits accounts, which can be portable, and which can provide employees with greater independence in selecting and maintaining employee benefits, regardless of their employer and/or employment status.

In any and/or all of the herein described embodiments, the employee or administrator can communicate or correspond with the central processing computer system 10 and/or any of the respective provider computer systems 11-18 with the communication or correspondence being performed with electronic mail transmissions, facsimile transmissions, electronic form submission and/or transmission techniques and/or any other method or means for transmitting correspondence or data and/or information in a network environment. The employee can also enter into contractual agreements directly with any given provider or providers so as to create a new agreement or change, modify, upgrade, enhance, or downgrade, any existing benefits agreement.

The central processing computer system 10, in the preferred embodiment, is located at a central location and is utilized in a network system, which in the preferred embodiment, is the Internet and/or the World Wide Web. In another preferred embodiment, the central processing computer system 10, and various communication devices 20, can be located in-house at an employer's location and can be utilized in an intranet/internet communication system. The various provider computer systems 11-18 can be located at any appropriate location and can be linked with the central processing computer system 10 and various communication devices 20 in the communication network. Any configuration or combination of configurations may be employed in any suitable network or configuration.

The various benefits pages, in the preferred embodiment, can be resident on the central processing computer system 10. The database 10H where any and all applicable data and/or information is stored, in the preferred embodiment, is dynamically linked with each of the respective databases located in the providers computer systems 11-18. In this manner, benefits data and/or information, updated at each of the respective provider computer systems 11-18, will be automatically updated in the database 10H.

The employee or administrator can access any of the provider computer systems 11-18, via the central processing computer system 10, in order to obtain other or additional benefits or provider information. In another preferred embodiment, the provider's page, or a portion thereof, can be resident on the respective provider computer and may be accessed via the home page resident on the central processing computer system 10.

The present invention also provides information concerning the various benefits with such information being continuously updated. In this manner, the employee or administrator can always obtain current benefits information, at any time and from any location, thereby dispensing with the need for having to search for, and maintain current records, or from having to seek same from employee records or from the employer's administrators or personnel department.

In the preferred embodiment, the apparatus may be menu-driven for facilitating simple use and operation. In any or all of the embodiments described herein, the apparatus can utilize Challenge Handshake Authentication Protocol (CHAP) and Transmission Control Protocol/Internet Protocol (TCP/IP).

Any and all communications between the employee or administrator and the various computer systems associated with the apparatus 1 can be secured by utilizing Security Socket Layer (SSL) technology or Point-to-Point Tunneling Protocol (PPTP) technology. Any other network communication security technology products, methods, or techniques, can also be utilized in conjunction with the apparatus and method of the present invention.

In another preferred embodiment, the present invention can be utilized so as to pool employees from different or smaller employers and/or employers which may have limited and/or disadvantageous bargaining positions in order for these employers to obtain benefits for their employees at more attractive rates.

The present invention allows benefits providers to communicate new programs, new benefits, and/or special programs and/or benefits discount offerings, to the employees who are serviced by the present invention. In this manner, benefits providers can offer or sell their respective services, policies and/or goods to the employees and/or to administrators.

The present invention, in a preferred embodiment, can provide notification of an employee's action to upgrade or change any of the benefits described herein so as to keep the employer informed about the status of benefits for each of its employees. Each of the benefits providers which are serviced by the apparatus of the present invention can also be provided with lists of employees covered under the various plans serviced by the apparatus along with the benefits provided to those employees.

The present invention can also provide benefits providers with information regarding employees who have recently upgraded benefits and/or which have taken advantage of benefits offers, employee discounts and/or buying services thereby providing the respective benefits providers with information and/or employees with whom the provider may communicate futures offerings.

The apparatus and method of the present invention can also provide an employee with the ability to select a different benefits provider from whom the employee can obtain benefits. In this manner, the employee may utilize monies provided by his or her employer, for a particular benefit or benefits, in order to obtain benefits from another benefits provider. The present invention, by providing an apparatus which can act as a centralized benefits managing system for interacting with numerous benefits providers, can provide a means by which to bring any employee serviced by the apparatus with any benefits provider also serviced thereby. In this manner, an employee can select a different benefits provider for a respective benefits coverage.

The present invention can be utilized in order for an employee to utilize monies and/or credits, which are provided by their respective employer for benefits under the employment relationship, in order to select and obtain a benefits plan or program which is tailored to the employee's needs and/or desires. In this regard, the present invention can be utilized in order to provide employee benefit plans or programs which can be independent of the employer provided benefits plan or program.

By allowing an employee to obtain a benefits plan or program, which is independent of the employer, the present invention can be utilized in order to provide individual benefits accounts which can be portable so that the individual employee may take his or her benefits plan or program from job to job and/or retain his benefits through periods of unemployment, in retirement and/or in periods between jobs.

The individual benefits account can be created when an employee receives benefits from a current employer. Once the employee's benefits have been entered into the central processing computer system 10 and the relationships between the employee and the various benefits providers have been established, the present invention will allow the employee to maintain the relationship with each benefits provider. In this regard, if an employee should decide to leave the employ of an employer, he or she may elect to retain benefits with any of his or her benefits providers.

The election to maintain a relationship with a benefits provider typically will require that the employee pay the benefits provider(s) for these benefits. The employee may then decide to make payment to the benefits provider(s) by either utilizing funds provided specifically for this purpose by a new employer and/or with individual funds. In this regard, the new employer, may simply provide the employee with funds for the employee's own benefits as part of the employee's compensation package. In some instances, the employee may have benefit funds remaining which he or she may elect to take as additional compensation or the employee may have to utilize individual funds in order to make up for any shortage in employer provided benefits funds.

In this manner, the present invention can be utilized to provide employee benefits independently of an employment relationship and to provide individual benefits and/or benefits accounts which can be portable from one employment relationship to another and which can be maintained by the employee during periods of unemployment, non-employment, retirement, or in between jobs. The individual benefits accounts provides an employee with benefits continuity and stability, for the employee and any dependents, and can relieve an employer of the expenses and inconvenience of having to set up and maintain benefits accounts for employees.

As noted above, the employee can pay for and/or purchase the benefits in his or her individual benefits account in whole or in part with funds, monies and/or credits provided by his or her employer during times of employment and/or with personal funds or monies during periods of unemployment or retirement. The employee, as in any of the herein-described embodiments, can change, modify, upgrade, or downgrade, any of his or her benefits and interact with any of the benefits providers in the manners described herein.

The present invention can also provide informational services, related to employee benefits, to the employee or administrator in various areas, including law, medicine, dentistry, accounting, and tax planning, etc.

The present invention also provides an apparatus and method for facilitating communication between various benefits providers. The present invention can also be utilized to allow various providers, such as doctors, physicians and other healthcare providers to confer and share information about an employee. In instances when an employee may need an authorized referral for a physician or other healthcare provider, the authorized referral may be provided from the referring provider to the referred to provider via the communication system and apparatus of the present invention. In this manner, referrals can be documented by the apparatus of the present invention for insurance purposes.

In another embodiment of the present invention, the central processing computer system 10 can be associated with, and/or be utilized by, a benefits providing institution and/or a benefits management institution in order to provide the services described herein. The central processing computer system 10 can also be utilized by brokers and/or dealers of the various employee benefits, insurance plans or programs, pension plans or programs, retirement plans or programs, employee discount and/or buying services plans or programs, etc. which are described herein.

In another preferred embodiment of the present invention, as well as in any and/or all of the embodiments described herein, the present invention can be utilized in conjunction with intelligent agents, software agents and/or mobile agents. Applicant hereby incorporates by reference herein the subject matter of the *Agent Sourcebook. A Complete Guide to Desktop. Internet and Intranet Agents*, by Alper Caglayan and Colin Harrison, Wiley Computer Publishing, 1997 Applicant also incorporates by reference herein the subject matter of *Cool Intelligent Agents For The Net*, by Leslie L. Lesnick with Ralph E. Moore, IDG Books Worldwide, Inc. 1997.

Intelligent agents can be utilized in any of the embodiments described herein in order to obtain information for an employee, an administrator or any of the various providers described herein.

An intelligent agent can act on behalf of the employee or administrator to obtain information on benefits and/or benefits information availability, status of benefits, status of benefits claims, and information about benefits providers, etc. An intelligent agent(s) can also be empowered to act for the employee or administrator so as to request benefits and/or benefits information, request services, purchase or order benefits and/or goods and/or services provided via the benefits plan or program.

An intelligent agent(s) can be programmed to perform any action and/or activity described herein for, or on behalf of, the employee, the administrator, or any of the various benefits providers. An intelligent agent can also be programmed to report the results of its findings and/or its actions taken to the respective employee, administrator, or benefits provider.

The employee, or administrator, can utilize an intelligent agent(s) in order to find, locate and/or obtain employee benefits and/or employee benefits information by requesting and/or instructing an intelligent agent(s) to do so. The employee may also request or instruct an intelligent agent(s) to find, locate and/or obtain information regarding his or her employment status and benefits which are provided to the employee.

The employee may request and/or instruct an intelligent agent(s) to find, locate and/or obtain, information, instructions and/or explanations regarding benefits, instructions for obtaining and claiming benefits. An intelligent agent(s) may also be deployed by the employee or administrator in order to make benefit elections or changes to benefits, to change investments in savings, pension and retirement accounts, to apply for additional benefits, and to file claims for health insurance, disability, or life insurance benefits.

The employee or administrator, can also utilize an intelligent agent(s) with instructions and/or authorizations to make purchases and/or place orders in connection with any of the employee discount programs and/or buying services provided as part of the employee benefits plan or program. The employee or administrator may utilize and/or deploy an intelligent agent(s) in order to obtain, to access, and/or to take advantage of, any and all employee benefits and/or employee benefits information which are made available under the employee benefits plan or program.

The employee or administrator may utilize and/or deploy an intelligent agent(s) at any time and from any location.

In the preferred embodiment, the employee benefits data and/or information can be accessed by an intelligent agent(s) by accessing the central processing computer system 10, which services the particular employee benefits plan or program, via the communication device 20.

The employee, or administrator, can utilize an intelligent agent(s) in order to obtain personnel information which can include the employee's name, address, social security number, date of birth, date of hire, payroll information, salary information, payroll withholdings and deductions information, tax exemption status, company stock account, stock options account, and/or equity interest account, if any, which the employee may hold in the company.

An intelligent agent(s) can also be utilized in order to obtain payroll, withholding and deduction information which can include the number of dependents, federal withholding taxes, state withholding taxes, local withholding taxes, social security taxes, disability taxes, disability withholding taxes, retirement deductions, pension deductions, IRA deductions, 401K deductions, SEP deductions, savings deductions, savings bond deductions, stock purchase plan deductions, employer held savings accounts, credit union deductions, etc.

An intelligent agent(s) can also be utilized in order to obtain information regarding tuition reimbursement programs, educational assistance programs, child care or day care programs as well as information regarding in-house training courses, training and educational courses set up outside the company, as well as schedules, course descriptions and registration information.

The employee can register for classes, by utilizing an intelligent agent(s), for any of the above courses and/or programs on-line and may do so via e-mail or via subscription forms which can be filed electronically via the communication device 20.

The employee can also utilize an intelligent agent(s) in order to request tuition reimbursement and in order to expenses account information.

An intelligent agent(s) can also be utilized in order to obtain information regarding company announcements, company calendars and/or schedules, personnel directories, and/or in-house job postings, etc. The employee or administrator can utilize an intelligent agent(s) in order to communicate with other employers, and/or to apply for in-house job openings.

The employee or administrator can also utilize an intelligent agent(s) in order to obtain information regarding life insurance benefits, disability insurance benefits, pension benefits, credit union and/or banking services benefits, retirement benefits and information regarding employee discounts and/or buying services. An intelligent agent(s) can be utilized in order to obtain information explaining the employee's pension benefits including vested and/or nonvested interests.

In any of the herein-described embodiments, an intelligent agent(s) can be deployed from the communication device 20.

The employee or administration can also utilize and/or deploy an intelligent agent(s) in order to obtain any employee benefits and/or employee benefits information, submit changes to benefits, submit benefits claims, register and/or subscribe to any of the employee benefits described herein, and/or make inquiries and/or status inquiries regarding employee benefits and/or employee benefits claims.

The employee can also utilize an intelligent agent(s) in order to transmit messages to the employer via e-mail transmission, facsimile transmission, electronic form submission or transmission, and/or by any other communication means, in order to allow the employee make changes to any of his or her employee benefits.

The employee can also utilize an intelligent agent(s) in order to effect any changes and/or modifications to any of the data and/or information described herein, on-line via the communication device 20.

The employee or administrator can utilize an intelligent agent(s) which can be dedicated to each provider or coverage type and which can obtain detailed explanations of the coverage and/or benefits provided, applicable deductibles or co-payments under the plan, instructions for obtaining benefits and/or directories and/or listings of providers, etc.

The employee can also utilize an intelligent agent(s) in order to select a primary care provider, if applicable, for each of the various benefits provided. The employee can also utilize an intelligent agent(s) in order to change primary care provider(s) and to request referral authorizations for specialists. The employee can also utilize intelligent agent(s) in order to submit claims on-line and check the status of claims which are pending.

The employee may also utilize an intelligent agent(s) in order to communicate directly with the health care benefits provider(s). The employee can also utilize an intelligent agent(s) in order to purchase upgraded benefits and/or change coverages, directly from the benefits provider, on-line via the communication device 20, in order to receive enhanced and/or upgraded benefits.

The employee or administrator can utilize an intelligent agent(s) in order to obtain detailed explanations of the benefits provided, instructions and/or information for obtaining and/or claiming benefits, information regarding filing a disability insurance claim, applicable deductibles and/or co-payments under the plan, directories and/or listings of individuals, doctors and/or other individuals and/or entities which have to be notified and/or contacted in order to file a disability insurance claim.

The employee, an administrator, or an employee's representative, can also utilize an intelligent agent(s) in order to submit life insurance claims and to check the status of claims which are currently pending, on-line via the communication device 20.

The employee can also utilize an intelligent agent(s) to communicate directly with the life insurance provider.

The employee can also utilize an intelligent agent(s) in order to purchase upgraded benefits directly from the provider or carrier, on-line via the communication device 20, in order to receive enhanced and/or upgraded life insurance benefits.

The employee can utilize an intelligent agent(s) in order to access account balances, to authorize or terminate payroll deductions into his or her account or accounts, to order checks, to make payments, to stop payments, to apply for loans and/or mortgages, to purchase certificates of deposits, bonds etc., as well as to perform any banking and/or savings activity, on-line and via the communication device 20.

The employee can also utilize an intelligent agent(s) in order to obtain financial advice, to obtain information regarding benefits offered by the credit union and/or banking services providers, to obtain special rate loans offered to employees, to apply for mortgages, to purchase stocks, bonds, mutual funds, savings bonds, etc., as well as to perform other savings and/or financial transactions with the credit union and/or banking services provider(s).

In any of the herein-described embodiments, the intelligent agent(s) can be utilized in the following manner. The employee, administrator, benefits provider, and/or central processing computer system operator, can request and/or instruct the intelligent agent(s) to perform a task and/or obtain information. The intelligent agent(s) will them be deployed to perform its task. Once the intelligent agent(s) has completed the task, the intelligent agent(s) will report the fact that the task has been completed, as well as the result(s) and/or outcome(s) of the task, along with any information related thereto, to the respective employee, administrator, benefits provider, and/or central processing computer system operator, on whose behalf the intelligent agent(s) acted.

The present invention can be utilized in order to provide employee benefits and/or employee benefits information for any number of, or for a plurality of, employers and employees.

In any of the embodiments described herein, any and all benefits requests forms, benefits information request forms, claims submission and/or request forms, claims status forms, and/or any other forms which may be needed in order to obtain employee benefits and/or employee benefits information, can be obtained from the central processing computer system 10 and/or from any of the respective provider computer systems 11-18. Any of the above forms can also be submitted via the communication device 20 over the communication network.

As noted above, the apparatus and method of the present invention, in any and/or all of the embodiments described herein, can be utilized so as to manage, administer, process information regarding, and/or provide any type of employee benefits, employee benefits services, employee benefits information, and/or human resource functions. As further noted above, Applicant hereby incorporates by reference herein the subject matter of *The Handbook of Employee Benefits*, Fourth Edition, Jerry S. Rosenbloom, McGraw-Hill, 1996 which describes a wide range of employee benefits and/or human resource functions which can also be managed, administered and/or processed, by the apparatus and method of the present invention.

In any and/or all of the embodiments described herein, the central processing computer 10, and/or any other computer or computer system linked thereto and/or associated therewith, can be utilized as an outsourcing entity and/or as any other type of agent and/or representative, so as process the payrolls, benefits payments, deferred income savings plans such as 401K plans or programs and/or other deferred income savings plans or programs, pension plans, etc., for any of the employers, employees, and/or other entities which utilize the present invention.

The central processing computer 10, and/or any other computer or computer system linked thereto and/or associated therewith, can also be utilized as an outsourcing entity and/or as any other type of agent and/or representative, so as to provide outsource processing of any human resource function and/or any other function which can or may be performed by a human resource department.

In any and/or all of the embodiments described herein, the central processing computer 10, and/or any other computer and/or computer system linked thereto or associated therewith, can also administer and/or manage financial accounts for any of the employers, employees, benefits providers, and/or any another party described herein. In this manner, the central processing computer 10 or other computer, can also manage and/or administer financial, bank, savings and/or checking accounts, for and/or on behalf of, make payments for and/or on behalf of, and/or receive payments for and/or on behalf of, any of the employers, employees, benefits providers, and/or any other party described herein. In this manner, the central processing computer 10, and/or any computer associated therewith, can also be utilized to make payments to benefits providers and/or to employees, to make benefits claims payments to employers and/or employees, to receive benefits claim payments for and/or on behalf of employees and/or employers, and/or to make or receive payments of any kind which may arise in an employer/employee, employer/benefit provider, and/or employee/benefit provider, environment and/or scenario.

In any and/or all of the embodiments described herein, the central processing computer 10, and/or any computer or computer system linked thereto and/or associated therewith, can also serve as a clearinghouse where any and/or all of the benefits providers described herein can post and/or advertise benefits, benefits packages, benefits pricing, and/or any information related thereto and/or associated therewith, which they offer. The postings, offerings and/or information, can be made available to any of the employers and/or employees described herein. Any of the benefits which are posted and/or offered via the central processing computer 10 and/or via the apparatus 1 of the present invention, can be purchased via the central processing computer 10, and/or associated computer or computer system, and/or via the apparatus 1 of the present invention. In this manner, any of the benefits described herein may be purchased from the respective benefits provider via the central processing computer 10, via any computer and/or computer system linked to and/or associated therewith, and/or via the apparatus 1 of the present invention.

In any and/or all of the embodiments described herein, the central processing computer 10, and/or any computer or computer system linked thereto and/or associated therewith, can be utilized to post requests for benefits, benefits needs, benefits requirements, and/or requests for benefits information, for any of the employers and/or employees or individuals described herein. In this manner, a benefits provider or benefits providers can review these posted requests, needs and/or requirements, and offer benefits and/or benefits packages directly to these employers, employees and/or individuals. In this manner, the present invention can be utilized by benefits providers to identify prospective customers and/or clients and to sell and/or offer to sell benefits and/or benefits packages directly to these employers, employees and/or individuals.

In any and/or all of the embodiments described herein, the central processing computer 10, and/or any computer and/or computer system linked thereto and/or associated therewith, can be programmed to match the benefits needs of the employers, employees, and/or individuals described herein with the benefits postings and/or benefits packages postings of any of the benefits providers described herein.

In any and/or all of the embodiments described herein, the database 10H, and/or any other database of any computer and/or computer system linked with the central processing computer 10 and/or associated therewith, can include the benefits, benefits packages, benefits pricing, and/or advertisements, which are posted and/or advertised by the benefits providers, as well as any of the benefits requirements and/or needs of any of the employers, employees and/or individuals described herein. The apparatus 1 of the present invention can also serve as, or provide, a clearinghouse or hub for selling and/or buying any and/or all of the employee benefits described herein as well an any good or service which can be offered in commerce by and/or between any of the benefits providers, employers, employees and/or individuals described herein.

In any and/or all of the embodiments described herein, the central processing computer 10 can provide notification, electronically, conventionally and/or otherwise, to any of the benefits providers, employers, employees and/or individuals, described herein, informing the respective party of changes to benefits, changes to, and/or activities regarding, benefits accounts, the offering of benefits which may be of interest to an employer, employee and/or individual, the posting of an offer to sell, and/or an advertisement for, benefits and/or benefits packages, the posting of benefits information, the posting of a need, request, or requirement, to buy and/or to obtain benefits, benefits packages, and/or benefits information, by, or which may be of interest to, any of the respective parties, individuals, employers, employees and/or benefits providers described herein.

The central processing computer 10 can also be utilized to provide notification of the making of a payment and/or the receipt of payment for and/or on behalf of any of the respective parties, individuals, employers, employees and/or benefits providers, described herein, the matching, or potential matching, of a benefit need with a benefit offering, the payment and/or receipt of contributions to a deferred income savings plan account, any other deferred income savings plan account, and/or a pension account or fund, the payment of benefit claims, and/or any other information, occurrence and/or event, which is, or which may be, of interest to any of the respective parties, individuals, employers, employees and/or benefits providers described herein.

The central processing computer 10 can also provide notification of, and/or provide account security regarding, any transaction which can occur on, for, and/or regarding, any of the financial accounts, belonging to, and/or managed and/or administered for, any of the respective parties, individuals, employers, employees and/or benefits providers described herein. Applicant hereby incorporates by reference herein the subject matter of U.S. Pat. No. 5,878,337 which teaches a transaction security apparatus and method. Applicant also hereby incorporates by reference herein the subject matter of U.S. Pat. No. 5,903,830 which teaches a transaction security apparatus and method.

In any and/or all of the embodiments described herein, the apparatus and method of the present invention can provide links to any goods and/or service providers who or which may be of interest to any of the respective parties, individuals, employers, employees and/or benefits providers described herein. In this manner, the present invention can provide links to attorneys, accountants, management consultants, security firms, recruiters, employment agencies, insurance providers, financial institutions, and/or the providers of any goods and/or services which may be the subject of commerce and/or which may be of interest to and/or needed by any of the respective parties, individuals, employers, employees and/or benefits providers described herein. In this manner, the central processing computer 10 and/or the apparatus 1 can serve as a clearinghouse and/or as a hub for providing business to business commerce and/or transactions.

In any and/or all of the embodiments described herein, any of the respective databases of any of the respective computers, the central processing computer(s) 10, the respective benefits provider computers 12, 13, 14, 15, 16, 17, 18, the employer computer(s) 11, and/or the communication device(s) 20, described herein, can and/or will contain any and/or all of the data and/or information needed and/or desired for offering any of the functions and/or services described herein as being provided and/or as being performed by the apparatus and method of the present invention.

In any and/or all of the embodiments described herein, any notification by, and/or any communication between, any of the parties described herein, which can be provided and/or which can be facilitated by the apparatus 1 of the present invention, and/or by any of the central processing computer(s) 10, the employer computer(s) 11, the communication device(s) 20, and/or any of the various provider computers 12, 13, 14, 15, 16, 17, 18, can be effected by electronic mail (e-mail) transmission(s), electronic transmission(s), facsimile transmission(s), telephone call(s), telephone message(s), voice message(s), pager message(s), beeper message(s), letter(s), physical mail, and/or via any other electronic and/or conventional communication method or technique.

Any e-mail messages and/or electronic transmissions can contain links and/or hyperlinks to the sending party and/or to a third party. For example, an e-mail message notifying an employer and/or an employee or individual that a certain benefit is available may contain a link or hyperlink to the central processing computer 10 and/or to the respective benefit provider and benefit provider computer.

In any and/or all of the embodiments described herein, the apparatus and method of the present invention can be utilized in conjunction with electronic power of attorney forms and/or any other electronic authorization, electronic signature, and/or digital signature, technologies, methods, and/or techniques, in order to facilitate the filing of authenticated forms and/or documents, including but not limited to, electronic medical, dental, or health, claim forms, electronic insurance claim forms, electronic financial transaction forms and/or financial claim forms, forms for effecting commerce for any good or service such as order forms, forms for offering and/or for requesting benefits and/or services, and/or for effecting any communication and/or transmission which would normally require an authentication, a signature, and/or any other authenticating information.

In any and/or all of the embodiments described herein, the central processing computer(s) 10, as well as any and/or all of the employer computers 11, the provider computers 12-18, and/or the communication devices 20, can be programmed to perform any of the respective operations, processing, and/or functions, described herein, as well as can be programmed for self-activation, self-operation, automatic activation, and/or automatic operation.

While the present invention has been described and illustrated in various preferred and alternate embodiments, such descriptions are merely illustrative of the present invention and are not to be construed to be limitations thereof. In this regard, the present invention encompasses all modifications, variations and/or alternate embodiments, with the scope of the present invention being limited only by the claims which follow.

The invention claimed is:

1. A computer-implemented method, comprising:

receiving information regarding a selection of an employee benefit, wherein an employee or a benefit beneficiary is previously enrolled in the employee benefit or an employee or a benefit beneficiary is provided with the employee benefit without enrolling in the employee benefit, wherein the information regarding a selection of an employee benefit is received via, on, or over, at least one of the Internet and the World Wide Web;

processing the information regarding a selection of the employee benefit with a first processing device, wherein the first processing device is a computer or a computer system which is accessed via, on, or over, at least one of the Internet and the World Wide Web or which operates on or over at least one of the Internet and the World Wide Web;

receiving a request for an employee benefit or a claim for an employee benefit, wherein the request for an employee benefit or the claim for an employee benefit is received via, on, or over, at least one of the Internet and the World Wide Web;

processing the request for an employee benefit or the claim for an employee benefit with a the first processing device or with a second processing device using employee benefit information or employee benefits information, wherein the second processing device is a computer or a computer system which is accessed via, on, or over, at least one of the Internet and the World Wide Web or which operates on or over at least one of the Internet and the World Wide Web, wherein the employee benefit information or the employee benefits information comprises information regarding the employee and at least one of health insurance information, disability insurance information, life insurance information, employee discount information, buying service information, tuition reimbursement information, educational assistance program information, in-house training information, child care program information, day care program information, and stock option information;

determining with the first processing device or with the second processing device whether the employee benefit requested in the request for an employee benefit or the claim for an employee benefit is to be provided;

generating a message in response to the request for an employee benefit or the claim for an employee benefit, wherein the message is generated by the first processing device or by the second processing device, and further wherein the message contains information indicating that at least one of a health insurance benefit, a disability insurance benefit, a life insurance benefit, an employee discount benefit, a buying service benefit, a tuition reimbursement benefit, an educational assistance program benefit, an in-house training benefit, a child care program benefit, a day care program benefit, and a stock option benefit, is provided or will be provided in response to the request for an employee benefit or the claim for an employee benefit; and transmitting the message to a communication device associated with at least one of the employee, the benefit beneficiary, an employer, and a benefit administrator, wherein the message is transmitted to the communication device via, on, or over, at least one of the Internet and the World Wide Web.

2. The computer-implemented method of claim 1, further comprising:
providing the employee benefit requested or claimed in the request for an employee benefit or the claim for an employee benefit if the message contains information indicating that the at least one of a health insurance benefit, a disability insurance benefit, a life insurance benefit, an employee discount benefit, a buying service benefit, a tuition reimbursement benefit, an educational assistance program benefit, an in-house training benefit, a child care program benefit, a day care program benefit, and a stock option benefit, will be provided.

3. The computer-implemented method of claim 1, further comprising:
processing information regarding a registration for a second employee benefit or a subscription to a second employee benefit.

4. The computer-implemented method of claim 1, further comprising:
processing a request for a status of the request for an employee benefit or the claim for an employee benefit;
generating a second message in response to the request for a status of the request for an employee benefit or the claim for an employee benefit; and
transmitting the second message to the communication device or to a second communication device associated with the at least one of the employee, the benefit beneficiary, an employer, and a benefit administrator.

5. The computer-implemented method of claim 1, further comprising:
processing information regarding a purchase of an enhanced employee benefit or an upgraded employee benefit.

6. The computer-implemented method of claim 1, further comprising:
processing information regarding a purchase of a second employee benefit or a purchase of at least one of a good, a product, and a service, pursuant to a second employee benefit.

7. The computer-implemented method of claim 1, further comprising:
processing information regarding a change to the employee benefit or to a second employee benefit.

8. The computer-implemented method of claim 1, wherein the communication device is at least one of a telephone, a handheld computer, and a personal communication device.

9. The computer-implemented method of claim 1, wherein the communication device is a television or an interactive television.

10. The computer-implemented method of claim 1, wherein the communication device is a wireless device.

11. The computer-implemented method of claim 1, wherein the communication device is a kiosk.

12. The computer-implemented method of claim 1, wherein the computer-implemented method is also performed or utilized on or over an intranet.

13. The computer-implemented method of claim 1, wherein the first processing device or the second processing device is at least one of a central processing unit, a computer in a network, a server computer, and an Internet server computer.

14. The computer-implemented method of claim 1, wherein the employee benefit information or the employee benefits information is at least one of automatically updated and automatically updated in real-time.

15. The computer-implemented method of claim 1, wherein the employee benefit information or the employee benefits information is associated with an independent contractor relationship.

16. The computer-implemented method of claim 1, further comprising:
processing information regarding a purchase pursuant to an employee discount benefit or a buying service benefit.

17. The computer-implemented method of claim 1, further comprising:
processing information regarding a registration for a class or a course.

18. The computer-implemented method of claim 1, further comprising:
processing information regarding at least one of a selection of a primary care provider, a request for a referral authorization for a specialist, a status of a health insurance claim, a purchase of a health insurance benefit, a change in a health insurance coverage, a status of a disability insurance claim, a purchase of a disability insurance benefit, a change in a disability insurance coverage, a status of a life insurance claim, a purchase of a life insurance benefit, and a change in a life insurance coverage.

19. The computer-implemented method of claim 1, further comprising:
processing information regarding at least one of a placing of an order with a goods provider or a service provider, a registration with a goods provider or a service provider, a subscription to a goods provider or a service provider, and a status of a pending order.

20. The computer-implemented method of claim 1, further comprising:
providing information to the employer regarding a transaction between the employee or a second employee and at least one of a health insurance benefit provider, a disability insurance benefit provider, and a life insurance benefit provider.

21. The computer-implemented method of claim 1, wherein the first processing device or the second processing device is at least one of an employer computer, a health insurance provider computer, a disability insurance provider computer, a life insurance provider computer, a credit union or banking services provider computer, a pension benefit provider computer, a retirement benefit provider computer, and an employee discount provider computer or is linked to at least one of an employer computer, a health insurance provider computer, a disability insurance provider computer, a life insurance provider computer, a credit union or banking services provider computer, a pension benefit provider computer, a retirement benefit provider computer, and an employee discount provider computer.

22. The computer-implemented method of claim 1, further comprising:
processing information regarding at least one of accessing a credit union account balance or a bank account balance, authorizing or terminating a payroll deduction, ordering a check or checks, making a payment, stopping a payment, applying for a loan or a mortgage, purchasing a certificate of deposit or a bond, providing financial advice, providing information regarding a benefit offered by a credit union or a banking service provider, providing information regarding a special rate loan offered to an employee or employees, applying for a mortgage, purchasing at least one of a stock, a bond, and a mutual fund, providing a forecast for a savings account, providing information regarding a company stock purchase made through a company-sponsored plan, and providing information regarding a savings bond purchasing plan.

23. The computer-implemented method of claim 1, further comprising:
storing information regarding at least one of a benefit, a benefit package, and a benefit pricing, provided by a benefit provider, and information regarding a requirement for a benefit or a need for a benefit associated with the employer, a second employer, the employee or a second employee;
processing the information regarding the at least one of a benefit, a benefit package, and a benefit pricing, with the information regarding a requirement for a benefit or a need for a benefit;
identifying a benefit provider for providing at least one of a benefit and benefit information for the requirement for a benefit or for the need for a benefit;
generating a second message containing information regarding the benefit provider, wherein the second message contains information regarding at least one of a benefit, a benefit package, and a benefit pricing, provided by the benefit provider; and
transmitting the second message to the communication device or to a second communication device associated with at least one of the employer, a second employer, the employee, and a second employee.

24. The computer-implemented method of claim 1, further comprising:
receiving a request for employee benefit information;
processing the request for employee benefit information;
generating a second message in response to the request for employee benefit information; and
transmitting the second message to the communication device or to a second communication device associated with at least one of the employee, the benefit beneficiary, the employer, a benefit administrator, and a second employee.

25. The computer-implemented method of claim 24, wherein the second message contains a link or a hyperlink to a computer associated with the first processing device or with the second processing device or to a computer associated with a benefit provider.

26. The computer-implemented method of claim 24, wherein the second message contains a link to a computer associated with at least one of a health insurance benefit provider, a disability insurance benefit provider, a life insurance benefit provider, a pension benefit provider, a retirement benefit provider, an employee discount benefit provider, and a buying service benefit provider.

27. The computer-implemented method of claim 1, wherein the employee benefit information or the employee benefits information further comprises information regarding an employee benefit associated with the employee, wherein the employee benefit exists from a previous employment relationship with a previous employer and is maintained by the employee in a current employment relationship with the employer, wherein the employee benefit from the previous employment relationship is paid for or provided at least in part by the employer pursuant to the current employment relationship and is included in employee benefits provided to the employee by the employer.

28. The computer-implemented method of claim 1, wherein the employee benefit information or the employee benefits information further comprises information regarding an individual benefits account, wherein the individual benefits account exists independently of an employment relationship with the employer.

29. The computer-implemented method of claim 1, further comprising:
processing information for pooling employees from a plurality of employers to obtain an employee benefit or employee benefits for the employees of the plurality of employers.

30. The computer-implemented method of claim 1, further comprising:
providing information to the employer regarding a transaction between the employee and a benefit provider.

31. The computer-implemented method of claim 1, further comprising:
processing information for allowing the employee or a second employee to utilize monies or credits provided by the employer to obtain a second employee benefit from a benefit provider.

32. The computer-implemented method of claim 1, further comprising:
processing information for utilizing an employer-provided at least one of a fund, money, and a credit, to create an individual benefits account, wherein the individual benefits account exists independently of an employment relationship with the employer.

33. The computer-implemented method of claim 1, further comprising:
transmitting information regarding at least one of a change to a benefit, a change to a benefit account, an activity regarding a benefit account, an offering of a benefit, a posting of an offer to sell a benefit, an advertisement for a benefit, a posting of benefit information, a payment to a deferred income savings account or a pension account, and a payment of a benefit claim, to the communication device or to a second communication device associated with the at least one of the employee, the benefit beneficiary, an employer, and a benefit administrator.

34. The computer-implemented method of claim 1, further comprising:
utilizing at least one of an intelligent agent, a software agent, and a mobile agent, at least one of to obtain information regarding at least one of a benefit, benefit information availability, a status of a benefit, a status of a benefit claim, and a benefit provider, to request a benefit or benefits information, to request a service, to purchase a good or a service, to perform an action for or on behalf of at least one of the employee, the benefit beneficiary, an employer, a benefit administrator, and a benefit provider, to report a finding or an action taken, and to purchase a benefit.

35. The computer-implemented method of claim 1, further comprising:
transmitting at least one of a benefit request form, a benefit information request form, a claim submission form, and a claim status form, to the communication device or to a second communication device associated with the at least one of the employee, the benefit beneficiary, an employer, and a benefit administrator.

36. The computer-implemented method of claim 1, wherein the message is contained in or transmitted in at least one of a facsimile transmission, a telephone call, a telephone message, a voice message, a pager message, and a beeper message.

37. The computer-implemented method of claim 1, further comprising:
utilizing at least one of an electronic power of attorney form, an electronic authorization, an electronic signature, and a digital signature, to file at least one of a medical claim form, a dental claim form, a healthcare claim form, an insurance claim form, a financial transaction form, a financial claim form, a goods order form or a service order form, and a benefit request form.

38. The computer-implemented method of claim 1, wherein the message is transmitted to the communication device in real-time.

39. The computer-implemented method of claim 1, further comprising:
effectuating a payment pursuant to the employee benefit in response to the request for an employee benefit or the claim for an employee benefit or effectuating a payment pursuant to a second employee benefit in response to a second request for an employee benefit or a second claim for an employee benefit.

40. The computer-implemented method of claim 1, wherein the computer-implemented method is performed or utilized on or over a cable television network.

41. The computer-implemented method of claim 1, wherein the request for an employee benefit or the claim for an employee benefit is transmitted from the communication device or from a second communication device associated with the at least one of the employee, the benefit beneficiary, an employer, and a benefit administrator.

42. The computer-implemented method of claim 1, further comprising:
receiving a second request for an employee benefit or a second claim for an employee benefit, wherein the second request for an employee benefit or the second claim for an employee benefit is made by the employee or by a second employee pursuant to or under a second employee benefit;
processing the second request for an employee benefit or the second claim for an employee benefit;
generating a second message in response to the second request for an employee benefit or the second claim for an employee benefit, wherein the second message contains at least one of information regarding a providing of the employee benefit requested or claimed in the second request for an employee benefit or the second claim for an employee benefit or a providing of a payment pursuant to the employee benefit requested or claimed in the second request for an employee benefit or the second claim for an employee benefit, wherein the employee benefit requested or claimed in the second request for an employee benefit or the second claim for an employee benefit is a health insurance benefit; and
transmitting the second message to the communication device or to a second communication device associated with at least one of the employee, a second employee, the benefit beneficiary, the employer, and a benefit administrator.

43. The computer-implemented method of claim 1, further comprising:
receiving a second request for an employee benefit or a second claim for an employee benefit, wherein the second request for an employee benefit or the second claim for an employee benefit is made by the employee or by a second employee pursuant to or under a second employee benefit;
processing the second request for an employee benefit or the second claim for an employee benefit;
generating a second message in response to the second request for an employee benefit or the second claim for an employee benefit, wherein the second message contains at least one of information regarding a providing of the employee benefit requested or claimed in the second request for an employee benefit or the second claim for an employee benefit or a providing of a payment pursuant to the employee benefit requested or claimed in the second request for an employee benefit or the second claim for an employee benefit, wherein the employee benefit requested or claimed in the second request for an employee benefit or the second claim for an employee benefit is a disability insurance benefit; and
transmitting the second message to the communication device or to a second communication device associated with at least one of the employee, a second employee, the benefit beneficiary, the employer, and a benefit administrator.

44. The computer-implemented method of claim 1, further comprising:
receiving a second request for an employee benefit or a second claim for an employee benefit, wherein the second request for an employee benefit or the second claim for an employee benefit is made by the employee or by a second employee pursuant to or under a second employee benefit;
processing the second request for an employee benefit or the second claim for an employee benefit;
generating a second message in response to the second request for an employee benefit or the second claim for an employee benefit, wherein the second message contains at least one of information regarding a providing of the employee benefit requested or claimed in the second request for an employee benefit or the second claim for an employee benefit or a providing of a payment pursuant to the employee benefit requested or claimed in the second request for an employee benefit or the second claim for an employee benefit, wherein the employee benefit requested or claimed in the second request for an employee benefit or the second claim for an employee benefit is a life insurance benefit; and transmitting the second message to the communication device or to a second communication device associated with at least one of the employee, a second employee, the benefit beneficiary, the employer, and a benefit administrator.

45. The computer-implemented method of claim 1, further comprising:

receiving a second request for an employee benefit or a second claim for an employee benefit, wherein the second request for an employee benefit or the second claim for an employee benefit is made by the employee or by a second employee pursuant to or under a second employee benefit;

processing the second request for an employee benefit or the second claim for an employee benefit;

generating a second message in response to the second request for an employee benefit or the second claim for an employee benefit, wherein the second message contains at least one of information regarding a providing of the employee benefit requested or claimed in the second request for an employee benefit or the second claim for an employee benefit or a providing of a payment pursuant to the employee benefit requested or claimed in the second request for an employee benefit or the second claim for an employee benefit, wherein the employee benefit requested or claimed in the second request for an employee benefit or the second claim for an employee benefit is a pension benefit; and transmitting the second message to the communication device or to a second communication device associated with at least one of the employee, a second employee, the benefit beneficiary, the employer, and a benefit administrator.

46. The computer-implemented method of claim 1, further comprising:

receiving a second request for an employee benefit or a second claim for an employee benefit, wherein the second request for an employee benefit or the second claim for an employee benefit is made by the employee or by a second employee pursuant to or under a second employee benefit;

processing the second request for an employee benefit or the second claim for an employee benefit;

generating a second message in response to the second request for an employee benefit or the second claim for an employee benefit, wherein the second message contains at least one of information regarding a providing of the employee benefit requested or claimed in the second request for an employee benefit or the second claim for an employee benefit or a providing of a payment pursuant to the employee benefit requested or claimed in the second request for an employee benefit or the second claim for an employee benefit, wherein the employee benefit requested or claimed in the second request for an employee benefit or the second claim for an employee benefit is an employee stock ownership benefit; and transmitting the second message to the communication device or to a second communication device associated with at least one of the employee, a second employee, the benefit beneficiary, the employer, and a benefit administrator.

47. The computer-implemented method of claim 1, further comprising:

receiving a second request for an employee benefit or a second claim for an employee benefit, wherein the second request for an employee benefit or the second claim for an employee benefit is made by the employee or by a second employee pursuant to or under a second employee benefit;

processing the second request for an employee benefit or the second claim for an employee benefit;

generating a second message in response to the second request for an employee benefit or the second claim for an employee benefit, wherein the second message contains at least one of information regarding a providing of the employee benefit requested or claimed in the second request for an employee benefit or the second claim for an employee benefit or a providing of a payment pursuant to the employee benefit requested or claimed in the second request for an employee benefit or the second claim for an employee benefit, wherein the employee benefit requested or claimed in the second request for an employee benefit or the second claim for an employee benefit is a credit union benefit; and transmitting the second message to the communication device or to a second communication device associated with at least one of the employee, a second employee, the benefit beneficiary, the employer, and a benefit administrator.

48. The computer-implemented method of claim 1, further comprising:

receiving a second request for an employee benefit or a second claim for an employee benefit, wherein the second request for an employee benefit or the second claim for an employee benefit is made by the employee or by a second employee pursuant to or under a second employee benefit;

processing the second request for an employee benefit or the second claim for an employee benefit;

generating a second message in response to the second request for an employee benefit or the second claim for an employee benefit, wherein the second message contains at least one of information regarding a providing of the employee benefit requested or claimed in the second request for an employee benefit or the second claim for an employee benefit or a providing of a payment pursuant to the employee benefit requested or claimed in the second request for an employee benefit or the second claim for an employee benefit, wherein the employee benefit requested or claimed in the second request for an employee benefit or the second claim for an employee benefit is a profit sharing benefit; and transmitting the second message to the communication device or to a second communication device associated with at least one of the employee, a second employee, the benefit beneficiary, the employer, and a benefit administrator.

49. The computer-implemented method of claim 1, further comprising:
  receiving a second request for an employee benefit or a second claim for an employee benefit, wherein the second request for an employee benefit or the second claim for an employee benefit is made by the employee or by a second employee pursuant to or under a second employee benefit;
  processing the second request for an employee benefit or the second claim for an employee benefit;
  generating a second message in response to the second request for an employee benefit or the second claim for an employee benefit, wherein the second message contains at least one of information regarding a providing of the employee benefit requested or claimed in the second request for an employee benefit or the second claim for an employee benefit or a providing of a payment pursuant to the employee benefit requested or claimed in the second request for an employee benefit or the second claim for an employee benefit, wherein the employee benefit requested or claimed in the second request for an employee benefit or the second claim for an employee benefit is a retirement benefit; and
  transmitting the second message to the communication device or to a second communication device associated with at least one of the employee, a second employee, the benefit beneficiary, the employer, and a benefit administrator.

50. The computer-implemented method of claim 1, wherein the message contains information indicating that an employee discount benefit is provided or will be provided.

51. The computer-implemented method of claim 1, wherein the message contains information indicating that a buying service benefit is provided or will be provided.

52. The computer-implemented method of claim 1, wherein the message contains information indicating that a tuition reimbursement benefit is provided or will be provided.

53. The computer-implemented method of claim 1, wherein the message contains information indicating that an educational assistance program benefit is provided or will be provided.

54. The computer-implemented method of claim 1, wherein the message contains information indicating that an in-house training benefit is provided or will be provided.

55. The computer-implemented method of claim 1, wherein the message contains information indicating that a profit sharing benefit is provided or will be provided.

56. The computer-implemented method of claim 1, wherein the message contains information indicating that a child care program benefit is provided or will be provided.

57. The computer-implemented method of claim 1, wherein the message contains information indicating that a day care program benefit is provided or will be provided.

58. The computer-implemented method of claim 1, wherein the message contains information indicating that a stock option benefit is provided or will be provided.

59. The computer-implemented method of claim 1, wherein the message contains information indicating that a credit union benefit or an employee stock ownership benefit is provided or will be provided.

60. The computer-implemented method of claim 1, wherein the message contains information indicating that a health insurance benefit is provided or will be provided.

61. The computer-implemented method of claim 1, wherein the message contains information indicating that a disability insurance benefit is provided or will be provided.

62. The computer-implemented method of claim 1, wherein the message contains information indicating that a life insurance benefit is provided or will be provided.

63. The computer-implemented method of claim 1, wherein the communication device is a personal computer or a laptop computer.

64. The computer-implemented method of claim 1, wherein the communication device is a personal digital assistant.

65. The computer-implemented method of claim 1, wherein the message is contained in an electronic mail message or transmitted in an electronic mail message.

66. The computer-implemented method of claim 1, wherein the communication device is a personal computer or a laptop computer.

67. The computer-implemented method of claim 1, wherein the communication device is a personal digital assistant.

68. The computer-implemented method of claim 1, wherein the message is contained in an electronic mail message or transmitted in an electronic mail message.

69. A computer-implemented method, comprising:
  receiving information regarding a selection of an employee benefit, wherein an employee or a benefit beneficiary is previously enrolled in the employee benefit or an employee or a benefit beneficiary is provided with the employee benefit without enrolling in the employee benefit, wherein the information regarding a selection of an employee benefit is received via, on, or over, at least one of the Internet and the World Wide Web;
  processing the information regarding a selection of the employee benefit with a first processing device, wherein the first processing device is a computer or a computer system which is accessed via, on, or over, at least one of the Internet and the World Wide Web or which operates on or over at least one of the Internet and the World Wide Web;
  receiving a request for an employee benefit or a claim for an employee benefit, wherein the request for an employee benefit or the claim for an employee benefit is received via, on, or over, at least one of the Internet and the World Wide Web;
  processing the request for an employee benefit or the claim for an employee benefit with the first processing device or with a second processing device using employee benefit information or employee benefits information wherein the second processing device is a computer or a computer system which is accessed via, on, or over, at least one of the Internet and the World Wide Web or which operates on or over at least one of the Internet and the World Wide Web, wherein the employee benefit information or the employee benefits information comprises information regarding the employee and at least one of health insurance information, disability insurance information, life insurance information, sick time information, credit union benefit information, employee stock ownership benefit information, profit sharing benefit information, employee discount information, buying service information, tuition reimbursement information, educational assistance program information, in-house training information, child care program information, day care program information, and stock option information;

determining with the first processing device or with the second processing device whether the employee benefit requested in the request for an employee benefit or the claim for an employee benefit is to be provided;

generating a message in response to the request for an employee benefit or the claim for an employee benefit, wherein the message is generated by the first processing device or by the second processing device, and further wherein the message contains information indicating that at least one of a health insurance benefit, a disability insurance benefit, a life insurance benefit, a sick time benefit, a credit union benefit, an employee stock ownership benefit, a profit sharing benefit, an employee discount benefit, a buying service benefit, a tuition reimbursement benefit, an educational assistance program benefit, an in-house training benefit, a child care program benefit, a day care program benefit, and a stock option benefit, is provided or will be provided in response to the request for an employee benefit or the claim for an employee benefit; and transmitting the message to a communication device associated with at least one of the employee, the benefit beneficiary, an employer, and a benefit administrator, wherein the message is transmitted to the communication device via, on, or over, at least one of the Internet and the World Wide Web.

70. The computer-implemented method of claim 69, further comprising:

providing the employee benefit requested or claimed in the request for an employee benefit or the claim for an employee benefit if the message contains information indicating at least one of a health insurance benefit, a disability insurance benefit, a life insurance benefit, a sick time benefit, a credit union benefit, an employee stock ownership benefit, a profit sharing benefit, an employee discount benefit, a buying service benefit, a tuition reimbursement benefit, an educational assistance program benefit, an in-house training benefit, a child care program benefit, a day care program benefit, and a stock option benefit, is provided or will be provided.

71. The computer-implemented method of claim 69, further comprising:

processing information regarding a registration for a second employee benefit or a subscription to a second employee benefit.

72. The computer-implemented method of claim 69, further comprising:

processing a request for a status of the request for an employee benefit or the claim for an employee benefit;

generating a second message in response to the request for a status of the request for an employee benefit or the claim for an employee benefit; and transmitting the second message to the communication device or to a second communication device associated with the at least one of the employee, the benefit beneficiary, an employer, and a benefit administrator.

73. The computer-implemented method of claim 69, further comprising:

processing information regarding a purchase of an enhanced employee benefit or an upgraded employee benefit.

74. The computer-implemented method of claim 69, further comprising:

processing information regarding a purchase of a second employee benefit or a purchase of at least one of a good, a product, and a service, pursuant to a second employee benefit.

75. The computer-implemented method of claim 69, further comprising:

processing information regarding a change to the employee benefit or to a second employee benefit.

76. The computer-implemented method of claim 69, wherein the communication device is at least one of a personal computer, a laptop computer, a personal digital assistant, a telephone, a handheld computer, and a personal communication device.

77. The computer-implemented method of claim 69, wherein the communication device is a television or an interactive television.

78. The computer-implemented method of claim 69, wherein the communication device is a wireless device.

79. The computer-implemented method of claim 69, wherein the communication device is a kiosk.

80. The computer-implemented method of claim 69, wherein the first processing device or the second processing device is at least one of a central processing unit, a computer in a network, a server computer, and an Internet server computer.

81. The computer-implemented method of claim 69, wherein the employee benefit information or the employee benefits information is at least one of automatically updated and automatically updated in real-time.

82. The computer-implemented method of claim 69, wherein the employee benefit information or the employee benefits information is associated with an independent contractor relationship.

83. The computer-implemented method of claim 69, further comprising:

processing information regarding a purchase pursuant to an employee discount benefit or a buying service benefit.

84. The computer-implemented method of claim 69, further comprising:

processing information regarding a registration for a class or a course.

85. The computer-implemented method of claim 69, further comprising:

processing information regarding at least one of a selection of a primary care provider, a request for a referral authorization for a specialist, a status of a health insurance claim, a purchase of a health insurance benefit, a change in a health insurance coverage, a status of a disability insurance claim, a purchase of a disability insurance benefit, a change in a disability insurance coverage, a status of a life insurance claim, a purchase of a life insurance benefit, and a change in a life insurance coverage.

86. The computer-implemented method of claim 69, further comprising:

processing information regarding at least one of a placing of an order with a goods provider or a service provider, a registration with a goods provider or a service provider, a subscription to a goods provider or a service provider, and a status of a pending order.

87. The computer-implemented method of claim 69, further comprising:

providing information to the employer regarding a transaction between the employee or a second employee and at least one of a health insurance benefit provider, a disability insurance benefit provider, and a life insurance benefit provider.

88. The computer-implemented method of claim 69, wherein the first processing device or the second processing device at least one of an employer computer, a health insurance provider computer, a disability insurance provider computer, a life insurance provider computer, a credit union or banking services provider computer, a pension benefit provider computer, a retirement benefit provider computer, and an employee discount provider computer or is linked to at least one of an employer computer, a health insurance provider computer, a disability insurance provider computer, a life insurance provider computer, a credit union or banking services provider computer, a pension benefit provider computer, a retirement benefit provider computer, and an employee discount provider computer.

89. The computer-implemented method of claim 69, further comprising:
processing information regarding at least one of accessing a credit union account balance or a bank account balance, authorizing or terminating a payroll deduction, ordering a check or checks, making a payment, stopping a payment, applying for a loan or a mortgage, purchasing a certificate of deposit or a bond, providing financial advice, providing information regarding a benefit offered by a credit union or a banking service provider, providing information regarding a special rate loan offered to an employee or employees, applying for a mortgage, purchasing at least one of a stock, a bond, and a mutual fund, providing a forecast for a savings account, providing information regarding a company stock purchase made through a company-sponsored plan, and providing information regarding a savings bond purchasing plan.

90. The computer-implemented method of claim 69, further comprising:
storing information regarding at least one of a benefit, a benefit package, and a benefit pricing, provided by a benefit provider, and information regarding a requirement for a benefit or a need for a benefit associated with the employer, a second employer, the employee or a second employee;
processing the information regarding the at least one of a benefit, a benefit package, and a benefit pricing, with the information regarding a requirement for a benefit or a need for a benefit;
identifying a benefit provider for providing at least one of a benefit and benefit information for the requirement for a benefit or for the need for a benefit;
generating a second message containing information regarding the benefit provider, wherein the second message contains information regarding at least one of a benefit, a benefit package, and a benefit pricing, provided by the benefit provider; and
transmitting the second message to the communication device or to a second communication device associated with at least one of the employer, a second employer, the employee, and a second employee.

91. The computer-implemented method of claim 69, further comprising:
receiving a request for employee benefit information;
processing the request for employee benefit information;
generating a second message in response to the request for employee benefit information; and
transmitting the second message to the communication device or to a second communication device associated with at least one of the employee, the benefit beneficiary, the employer, a benefit administrator, and a second employee.

92. The computer-implemented method of claim 91, wherein the second message contains a link or a hyperlink to a computer associated with the first processing device or the second processing device or to a benefit provider computer.

93. The computer-implemented method of claim 69, wherein the message contains information indicating that at least one of a pension benefit and a retirement benefit is provided or will be provided.

94. The computer-implemented method of claim 69, wherein the message contains information indicating that at least one of a health insurance benefit, a disability insurance benefit, and a life insurance benefit, is provided or will be provided.

95. The computer-implemented method of claim 69, wherein the message contains information indicating that at least one of a vacation time benefit, a personal time benefit, and a sick time benefit, is provided or will be provided.

96. The computer-implemented method of claim 69, wherein the message contains information indicating that at least one of a credit union benefit, an employee stock ownership benefit, and a profit sharing benefit, is provided or will be provided.

97. The computer-implemented method of claim 69, wherein the message contains information indicating that at least one of an employee discount benefit, a buying service benefit, a child care program benefit, a day care program benefit, and a stock option benefit, is provided or will be provided.

98. The computer-implemented method of claim 69, wherein the message contains information indicating that at least one of a tuition reimbursement benefit, an educational assistance program benefit, and an in-house training benefit, is provided or will be provided.

99. The computer-implemented method of claim 69, further comprising:
providing a pension benefit or a retirement benefit or providing a payment pursuant to a pension benefit or a retirement benefit.

100. The computer-implemented method of claim 91, wherein the second message contains information regarding at least one of an employee discount, a buying service, and a buying service which participates in an employee benefit program.

101. The computer-implemented method of claim 91, wherein the second message contains a link to a computer associated with at least one of a health insurance benefit provider, a disability insurance benefit provider, a life insurance benefit provider, a pension benefit provider, a retirement benefit provider, an employee discount benefit provider, and a buying service benefit provider.

102. The computer-implemented method of claim 69, wherein the employee benefit information or the employee benefits information further comprises information regarding an employee benefit associated with an employee, wherein the employee benefit exists from a previous employment relationship and is maintained by the employee in a current employment relationship with the employer, wherein the employee benefit from the previous employment relationship with a previous employer is paid for or provided at least in part by the employer pursuant to the current employment relationship and is included in employee benefits provided to the employee by the employer.

103. The computer-implemented method of claim 69, wherein the employee benefit information or the employee benefits information further comprises information regarding an individual benefits account, wherein the individual benefits account exists independently of an employment relationship with the employer.

104. The computer-implemented method of claim 69, further comprising:
processing information for allowing the employee or a second employee to utilize monies or credits provided by the employer to obtain a second employee benefit from a benefit provider.

105. The computer-implemented method of claim 69, further comprising:
providing information to a benefit provider regarding any employee who has upgraded a benefit or utilized at least one of a benefit offer, an employee discount benefit, and a buying service benefit.

106. The computer-implemented method of claim 69, further comprising:
processing information for utilizing an employer-provided at least one of a fund, money, and a credit, to create an individual benefits account, wherein the individual benefits account exists independently of an employment relationship with the employer.

107. The computer-implemented method of claim 69, further comprising:
transmitting information regarding at least one of a change to a benefit, a change to a benefit account, an activity regarding a benefit account, an offering of a benefit, a posting of an offer to sell a benefit, an advertisement for a benefit, a posting of benefit information, a payment to a deferred income savings account or a pension account, and a payment of a benefit claim, to the communication device or to a second communication device associated with the at least one of the employee, the benefit beneficiary, an employer, and a benefit administrator.

108. The computer-implemented method of claim 69, further comprising:
utilizing at least one of an intelligent agent, a software agent, and a mobile agent, at least one of to obtain information regarding at least one of a benefit, benefit information availability, a status of a benefit, a status of a benefit claim, and a benefit provider, to request benefit information, to request a service, to purchase a good or a service, to perform an action for or on behalf of at least one of the employee, the benefit beneficiary, an employer, a benefit administrator, and a benefit provider, to report a finding or an action taken, and to purchase a benefit.

109. The computer-implemented method of claim 69, further comprising:
transmitting at least one of a benefit request form, a benefit information request form, a claim submission form, and a claim status form, to the communication device or to a second communication device associated with the at least one of the employee, the benefit beneficiary, an employer, and a benefit administrator.

110. The computer-implemented method of claim 69, wherein the message is contained or transmitted in at least one of an electronic mail transmission, an electronic transmission, a facsimile transmission, a telephone call, a telephone message, a voice message, a pager message, and a beeper message.

111. The computer-implemented method of claim 69, further comprising:
utilizing at least one of an electronic power of attorney form, an electronic authorization, an electronic signature, and a digital signature, to file at least one of a medical claim form, a dental claim form, a healthcare claim form, an insurance claim form, a financial transaction form, a financial claim form, a goods order form or a service order form, and a benefit request form.

112. The computer-implemented method of claim 69, wherein the message is transmitted to the communication device in real-time.

113. The computer-implemented method of claim 69, further comprising:
effectuating a payment pursuant to the employee benefit in response to the request for an employee benefit or the claim for an employee benefit or effectuating a payment pursuant to a second employee benefit in response to a second request for an employee benefit or a second claim for an employee benefit.

114. The computer-implemented method of claim 69, wherein the computer-implemented method is performed or utilized on or over a cable television network.

115. The computer-implemented method of claim 69, wherein the request for an employee benefit or the claim for an employee benefit is transmitted from the communication device or from a second communication device associated with the at least one of the employee, the benefit beneficiary, an employer, and a benefit administrator.

116. A computer-implemented method, comprising:
receiving information regarding a selection of an employee benefit, wherein an employee or a benefit beneficiary is previously enrolled in the employee benefit or an employee or a benefit beneficiary is provided with the employee benefit without enrolling in the employee benefit, wherein the information regarding a selection of an employee benefit is received via, on, or over, at least one of the Internet and the World Wide Web;
processing the information regarding a selection of the employee benefit with a first processing device, wherein the first processing device is a computer or a computer system which is accessed via, on, or over, at least one of the Internet and the World Wide Web or which operates on or over at least one of the Internet and the World Wide Web;
receiving a first request for an employee benefit or a first claim for an employee benefit, wherein the first request for an employee benefit or the first claim for an employee benefit is received via, on, or over, at least one of the Internet and the World Wide Web;
processing the first request for an employee benefit or the first claim for an employee benefit with the first processing device or with a second processing device using employee benefit information or employee benefits information wherein the second processing device is a computer or a computer system which is accessed via, on, or over, at least one of the Internet and the World Wide Web or which operates on or over at least one of the Internet and the World Wide Web, wherein the employee benefit information or the employee benefits information comprises at least one of health insurance information, disability insurance information, life insurance information, credit union benefit information, employee stock ownership benefit information, profit sharing benefit information, employee discount information, buying service information, tuition reimbursement information, educational assistance program information, in-house training information, child care program information, day care program information, and stock option information;

determining with the first processing device or with the second processing device whether the employee benefit requested in the first request for an employee benefit or the first claim for an employee benefit is to be provided;

generating a first message in response to the first request for an employee benefit or the first claim for an employee benefit, wherein the first message is generated by the first processing device or by the second processing device, and further wherein the first message contains information indicating that at least one of a health insurance benefit, a disability insurance benefit, a life insurance benefit, a credit union benefit, an employee stock ownership benefit, a profit sharing benefit, an employee discount benefit, a buying service benefit, a tuition reimbursement benefit, an educational assistance program benefit, an in-house training benefit, a child care program benefit, a day care program benefit, and a stock option benefit, is provided or will be provided in response to the first request for an employee benefit or the first claim for an employee benefit;

transmitting the first message to a communication device associated with at least one of the employee, the benefit beneficiary, an employer, and a benefit administrator, wherein the first message is transmitted to the communication device via, on, or over, at least one of the Internet and the World Wide Web;

receiving a second request for an employee benefit or a second claim for an employee benefit, wherein the second request for an employee benefit or the second claim for an employee benefit is made by the employee or by a second employee, and further wherein the second request for an employee benefit or the second claim for an employee benefit is a request or claim for at least one of a vacation time benefit, a personal time benefit, and a sick time benefit;

processing the second request for an employee benefit or the second claim for an employee benefit using at least one of vacation time information, personal time information, and sick time information;

generating a second message in response to the second request for an employee benefit or the second claim for an employee benefit, wherein the second message contains information indicating that at least one of a vacation time benefit, a personal time benefit, and a sick time benefit, is provided or will be provided; and transmitting the second message to the communication device or to a second communication device associated with at least one of the employee, the second employee, the benefit beneficiary, the employer, and a benefit administrator.

117. A computer-implemented method, comprising:

receiving information regarding a selection of an employee benefit, wherein an employee or a benefit beneficiary is previously enrolled in the employee benefit or an employee or a benefit beneficiary is provided with the employee benefit without enrolling in the employee benefit, wherein the information regarding a selection of an employee benefit is received via, on, or over, at least one of the Internet and the World Wide Web;

processing the information regarding a selection of the employee benefit with a first processing device, wherein the first processing device is a computer or a computer system which is accessed via, on, or over, at least one of the Internet and the World Wide Web or which operates on or over at least one of the Internet and the World Wide Web;

receiving a first request for an employee benefit or a first claim for an employee benefit, wherein the first request for an employee benefit or the first claim for an employee benefit is received via, on, or over, at least one of the Internet and the World Wide Web;

processing the first request for an employee benefit or the first claim for an employee benefit with the first processing device or with a second processing device using employee benefit information or employee benefits information wherein the second processing device is a computer or a computer system which is accessed via, on, or over, at least one of the Internet and the World Wide Web or which operates on or over at least one of the Internet and the World Wide Web, wherein the employee benefit information or the employee benefits information comprises at least one of vacation time information, personal time information, sick time information, employee discount information, buying service information, tuition reimbursement information, educational assistance program information, in-house training information, child care program information, day care program information, credit union benefit information, employee stock ownership benefit information, profit sharing benefit information, and stock option information;

determining with the first processing device or with the second processing device whether the employee benefit requested in the first request for an employee benefit or the first claim for an employee benefit is to be provided;

generating a first message in response to the first request for an employee benefit or the first claim for an employee benefit, wherein the first message is generated by the first processing device or by the second processing device, and further wherein the first message contains information indicating that at least one of a vacation time benefit, a personal time benefit, a sick time benefit, an employee discount benefit, a buying service benefit, a tuition reimbursement benefit, an educational assistance program benefit, an in-house training benefit, a child care program benefit, a day care program benefit, a credit union benefit, an employee stock ownership benefit, a profit sharing benefit, and a stock option benefit, is provided or will be provided in response to the first request for an employee benefit or the first claim for an employee benefit;

transmitting the first message to a communication device associated with at least one of the employee, the benefit beneficiary, an employer, and a benefit administrator, wherein the first message is transmitted to the communication device via, on, or over, at least one of the Internet and the World Wide Web;

receiving a second request for an employee benefit or a second claim for an employee benefit, wherein the second request for an employee benefit or the second claim for an employee benefit is made by the employee or by a second employee, and further wherein the second request for an employee benefit or the second claim for an employee benefit is a request or claim for at least one of a health insurance benefit, a disability insurance benefit, and a life insurance benefit;

processing the second request for an employee benefit or the second claim for an employee benefit using at least one of health insurance information, disability insurance information, and life insurance information;

generating a second message in response to the second request for an employee benefit or the second claim for an employee benefit, wherein the second message contains information indicating that at least one of a health insurance benefit, a disability insurance benefit, and a life insurance benefit, is provided or will be provided, or indicating that a payment pursuant to at least one of a health insurance benefit, a disability insurance benefit, and a life insurance benefit, is provided or will be provided; and transmitting the second message to the communication device or to a second communication device associated with at least one of the employee, the second employee, the benefit beneficiary, the employer, and a benefit administrator.

118. A computer-implemented method, comprising:

receiving information regarding a selection of an employee benefit, wherein an employee or a benefit beneficiary is previously enrolled in the employee benefit or an employee or a benefit beneficiary is provided with the employee benefit without enrolling in the employee benefit, wherein the information regarding a selection of an employee benefit is received via, on, or over, at least one of the Internet and the World Wide Web;

processing the information regarding a selection of the employee benefit with a first processing device, wherein the first processing device is a computer or a computer system which is accessed via, on, or over, at least one of the Internet and the World Wide Web or which operates on or over at least one of the Internet and the World Wide Web;

receiving a first request for an employee benefit or a first claim for an employee benefit, wherein the first request for an employee benefit or the first claim for an employee benefit is received via, on, or over, at least one of the Internet and the World Wide Web;

processing the first request for an employee benefit or the first claim for an employee benefit with a the first processing device or with a second processing device using employee benefit information or employee benefits information wherein the second processing device is a computer or a computer system which is accessed via, on, or over, at least one of the Internet and the World Wide Web or which operates on or over at least one of the Internet and the World Wide Web, wherein the employee benefits information comprises at least one of vacation time information, personal time information, sick time information, credit union benefit information, employee stock ownership benefit information, and profit sharing benefit information, employee discount information, buying service information, tuition reimbursement information, educational assistance program information, in-house training information, child care program information, day care program information, and stock option information;

determining with the first processing device or with the second processing device whether the employee benefit requested in the first request for an employee benefit or the first claim for an employee benefit is to be provided;

generating a first message in response to the first request for an employee benefit or the first claim for an employee benefit, wherein the first message is generated by the first processing device or by the second processing device, and further wherein the first message contains information indicating that at least one of a vacation time benefit, a personal time benefit, a sick time benefit, a credit union benefit, an employee stock ownership benefit, a profit sharing benefit, an employee discount benefit, a buying service benefit, a tuition reimbursement benefit, an educational assistance program benefit, an in-house training benefit, a child care program benefit, a day care program benefit, and a stock option benefit, is provided or will be provided in response to the first request for an employee benefit or the first claim for an employee benefit;

transmitting the first message to a communication device associated with at least one of the employee, the benefit beneficiary, an employer, and a benefit administrator, wherein the first message is transmitted to the communication device via, on, or over, at least one of the Internet and the World Wide Web;

receiving a second request for an employee benefit or a second claim for an employee benefit, wherein the second request for an employee benefit or the second claim for an employee benefit is made by the employee for by a second employee, and further wherein the second request for an employee benefit or the second claim for an employee benefit is a request or claim for a pension benefit or a retirement benefit;

processing the second request for an employee benefit or the second claim for an employee benefit using pension benefit information or retirement benefit information;

generating a second message in response to the second request for an employee benefit or the second claim for an employee benefit, wherein the second message contains information indicating that a pension benefit or a retirement benefit is provided or will be provided, or indicating that a payment pursuant to a pension benefit or a retirement benefit is provided or will be provided; and transmitting the second message to the communication device or to a second communication device associated with at least one of the employee, the second employee, the benefit beneficiary, the employer, and a benefit administrator.

119. A computer-implemented method, comprising:

storing or processing information regarding a benefit provided to an employee pursuant to an employee benefit relationship between the employee and a benefit provider, wherein the benefit is at least one of a health insurance benefit, a disability insurance benefit, and a life insurance benefit, wherein the employee benefit relationship is established pursuant to or during a first employment relationship between the employee and a first employer;

storing or processing information for providing or maintaining the benefit provided to the employee pursuant to the employee benefit relationship pursuant to or during a second employment relationship between the employee and a second employer, wherein the second employment relationship is a current employment relationship, wherein the benefit provided pursuant to the employee benefit relationship is paid for or provided at least in part by the second employer in or pursuant to the second employment relationship and is included in employee benefits provided to the employee by the second employer;

receiving a request for information regarding the benefit provided pursuant to the employee benefit relationship which is paid for or provided at least in part by the second employer in or pursuant to the second employment relationship and which is included in employee benefits provided to the employee by the second employer;

processing the request for information regarding the benefit with a processing device using employee benefit information or employee benefits information wherein the processing device is a computer or a computer system which is accessed via, on, or over, at least one of the Internet and the World Wide Web or which operates on or over at least one of the Internet and the World Wide Web;

generating a message in response to the processing of the request for information regarding the benefit, wherein the message contains a response to the request for information regarding the benefit; and transmitting the message to a communication device associated with at least one of the employee, a benefit beneficiary, the second employer, and a benefit administrator, wherein the message is transmitted to the communication device via, on, or over, at least one of the Internet and the World Wide Web.

120. The computer-implemented method of claim 119, further comprising:

receiving a request for an employee benefit or a claim for an employee benefit;

processing the request for an employee benefit or the claim for an employee benefit;

generating a second message in response to the request for an employee benefit or the claim for an employee benefit; and transmitting the second message to the communication device.

121. The computer-implemented method of claim 120, wherein the second message contains information indicating that the employee benefit requested in the request for an employee benefit or the claim for an employee benefit is provided or will be provided.

122. The computer-implemented method of claim 120, further comprising:

providing the employee benefit requested or claimed in the request for an employee benefit or the claim for an employee benefit or providing a payment pursuant to the employee benefit requested or claimed in the request for an employee benefit or the claim for an employee benefit.

123. The computer-implemented method of claim 119, further comprising:

processing information regarding a registration for the benefit or a second benefit or processing information regarding a subscription to the benefit or a second benefit.

124. The computer-implemented method of claim 120, further comprising:

processing a request for a status of the request for an employee benefit or the claim for an employee benefit;

generating a third message in response to the request for a status of the request for an employee benefit or the claim for an employee benefit; and transmitting the third message to the communication device.

125. The computer-implemented method of claim 119, further comprising:

processing information regarding a purchase of an enhanced benefit or an upgraded benefit.

126. The computer-implemented method of claim 119, further comprising:

processing information regarding a purchase of an employee benefit or a purchase of at least one of a good, a product, and a service, pursuant to an employee benefit.

127. The computer-implemented method of claim 119, further comprising:

processing information regarding a change to the benefit or a change to a second benefit.

128. The computer-implemented method of claim 119, wherein the benefit is a health insurance benefit.

129. The computer-implemented method of claim 119, wherein the benefit is a disability insurance benefit.

130. The computer-implemented method of claim 119, wherein the benefit is a life insurance benefit.

131. The computer-implemented method of claim 119, wherein the communication device is at least one of a telephone, a handheld computer, and a personal communication device.

132. The computer-implemented method of claim 119, wherein the communication device is a television or an interactive television.

133. The computer-implemented method of claim 119, wherein the communication device is a wireless device.

134. The computer-implemented method of claim 119, wherein the communication device is a kiosk.

135. The computer-implemented method of claim 119, wherein the computer-implemented method is also performed or utilized on or over an intranet.

136. The computer-implemented method of claim 119, wherein the processing device is at least one of a central processing unit, a computer in a network, a server computer, and an Internet server computer.

137. The computer-implemented method of claim 119, wherein the information regarding a benefit is at least one of automatically updated and updated in real-time.

138. The computer-implemented method of claim 119, wherein the employee is an independent contractor.

139. The computer-implemented method of claim 119, further comprising:

processing information regarding a purchase pursuant to an employee discount benefit or a buying service benefit.

140. The computer-implemented method of claim 119, further comprising:

processing information regarding a registration for a class or a course or processing information regarding a request for a tuition reimbursement.

141. The computer-implemented method of claim 119, further comprising:

processing information regarding at least one of a selection of a primary care provider, a request for a referral authorization for a specialist, a status of a health insurance claim, a purchase of a health insurance benefit, a change in a health insurance coverage, a status of a disability insurance claim, a purchase of a disability insurance benefit, a change in a disability insurance coverage, a status of a life insurance claim, a purchase of a life insurance benefit, and a change in a life insurance coverage.

142. The computer-implemented method of claim 119, further comprising:

processing information regarding at least one of a placing of an order with a goods provider or a service provider, a registration with a goods provider or a service provider, a subscription to a goods provider or a service provider, and a status of a pending order.

143. The computer-implemented method of claim 119, further comprising:
providing information to the second employer regarding a transaction between the employee and at least one of a health insurance benefit provider, a disability insurance benefit provider, and a life insurance benefit provider.

144. The computer-implemented method of claim 119, wherein the processing device is linked to at least one of an employer computer, a health insurance provider computer, a disability insurance provider computer, a life insurance provider computer, a credit union or banking services provider computer, a pension benefit provider computer, a retirement benefit provider computer, and an employee discount provider computer.

145. The computer-implemented method of claim 119, further comprising:
storing information regarding at least one of a benefit, a benefit package, and a benefit pricing, provided by a benefit provider, and information regarding a requirement for a benefit or a need for a benefit associated with the employer or the employee or a second employee;
processing the information regarding the at least one of a benefit, a benefit package, and a benefit pricing, with the information regarding a requirement for a benefit or a need for a benefit;
identifying a benefit provider for providing at least one of a benefit and benefit information for the requirement for a benefit or for the need for a benefit;
generating a second message containing information regarding the benefit provider, wherein the second message contains information regarding at least one of a benefit, a benefit package, and a benefit pricing, provided by the benefit provider; and
transmitting the second message to the communication device or to a second communication device associated with at least one of the employer, the employee, and the second employee.

146. The computer-implemented method of claim 119, wherein the message contains a link or a hyperlink to a computer associated with the processing device or to a benefit provider computer.

147. The computer-implemented method of claim 119, further comprising:
storing or processing information regarding an individual benefits account, wherein the individual benefits account exists independently of the previous employment relationship or the current employment relationship.

148. The computer-implemented method of claim 119, further comprising:
processing information for pooling employees from a plurality of employers to obtain an employee benefit for the employees of the plurality of employers.

149. The computer-implemented method of claim 119, further comprising:
providing information to a benefit provider regarding the employee or a second employee who has upgraded a benefit or utilized at least one of a benefit offer, an employee discount benefit, and a buying service benefit.

150. The computer-implemented method of claim 119, further comprising:
processing information for allowing the employee or a second employee to utilize monies or credits provided by the second employer to obtain an employee benefit from a benefit provider, or processing information for allowing the employee or a second employee to utilize funds provided by the second employer to make a payment to a benefit provider.

151. The computer-implemented method of claim 119, further comprising:
processing information for establishing or creating an individual benefits account, wherein the individual benefits account exists independently of the previous employment relationship and the current employment relationship, and further wherein the employee pays for or purchases a benefit in whole or in part with at least one of funds, monies, and credits, provided by the first employer or the second employer.

152. The computer-implemented method of claim 119, further comprising:
utilizing at least one of an intelligent agent, a software agent, and a mobile agent, at least one of to obtain information regarding at least one of a benefit, benefit information availability, a status of a benefit, a status of a benefit claim, and a benefit provider, to request benefit information, to request a service, to purchase a good or a service, to perform an action for or on behalf of at least one of the employee, a benefit beneficiary, the first employer or the second employer, a benefit administrator, and a benefit provider, to report a finding or an action taken, and to purchase a benefit.

153. The computer-implemented method of claim 119, further comprising:
transmitting at least one of a benefit request form, a benefit information request form, a claim submission form, and a claim status form, to the communication device or to a second communication device associated with the at least one of the employee, a benefit beneficiary, the second employer, and a benefit administrator.

154. The computer-implemented method of claim 119, further comprising:
transmitting information regarding at least one of a change to a benefit, a change to a benefit account, an activity regarding a benefit account, an offering of a benefit, a posting of an offer to sell a benefit, an advertisement for a benefit, a posting of benefit information, a payment to a deferred income savings account or a pension account, and a payment of a benefit claim.

155. The computer-implemented method of claim 119, wherein the message is contained or transmitted in at least one of a facsimile transmission, a telephone call, a telephone message, a voice message, a pager message, and a beeper message.

156. The computer-implemented method of claim 119, further comprising:
utilizing at least one of an electronic power of attorney form, an electronic authorization, an electronic signature, and a digital signature, to file at least one of a medical claim form, a dental claim form, a healthcare claim form, an insurance claim form, a financial transaction form, a financial claim form, a goods order form or a service order form, and a benefit request form.

157. The computer-implemented method of claim 119, wherein the message is transmitted to the communication device in real-time.

158. The computer-implemented method of claim 119, further comprising:
effectuating a payment pursuant to the benefit in response to a request for the benefit or a claim for the benefit or a second benefit.

159. The computer-implemented method of claim 119, wherein the computer-implemented method is performed or utilized via, on, or over, a cable television network.

160. The computer-implemented method of claim 119, wherein the request for information regarding the benefit is transmitted from the communication device.

161. The computer-implemented method of claim 119, further comprising:
  storing information regarding an individual benefits account, wherein the individual benefits account is utilized by the employee to retain a benefit with a benefit provider independently of a previous employment relationship or the current employment relationship.

162. The computer-implemented method of claim 161, wherein the individual benefits account includes at least one of a health insurance benefit, a disability insurance benefit, a life insurance benefit, a pension benefit, and a retirement benefit.

163. The computer-implemented method of claim 119, wherein the communication device is a personal computer or a laptop computer.

164. The computer-implemented method of claim 119, wherein the communication device is a personal digital assistant.

165. The computer-implemented method of claim 119, wherein the message is contained in an electronic mail message or transmitted in an electronic mail message.

166. A computer-implemented method, comprising:
  storing or processing information regarding a benefit provided to an employee pursuant to an employee benefit relationship between the employee and a benefit provider, wherein the benefit is at least one of a health insurance benefit, a disability insurance benefit, and a life insurance benefit, wherein the employee benefit relationship is established pursuant to or during a first employment relationship between the employee and a first employer;
  storing or processing information for providing or maintaining the benefit provided to the employee pursuant to the employee benefit relationship pursuant to or during a second employment relationship between the employee and a second employer, wherein the second employment relationship is a current employment relationship, wherein the benefit provided pursuant to the employee benefit relationship is paid for or provided at least in part by the second employer in or pursuant to the second employment relationship and is included in employee benefits provided to the employee by the second employer;
  receiving a request for information regarding the benefit provided pursuant to the employee benefit relationship which is paid for or provided at least in part by the second employer in or pursuant to the second employment relationship and which is included in employee benefits provided to the employee by the second employer, and further wherein the request for information regarding the benefit is transmitted from a communication device associated with at least one of the employee, a benefit beneficiary, the second employer, and a benefit administrator;
  processing the request for information regarding the benefit with a processing device, wherein the processing device is a computer or a computer system which is accessed via, on, or over, at least one of the Internet and the World Wide Web or which operates on or over at least one of the Internet and the World Wide Web;
  generating a message in response to the processing of the request for information regarding the benefit, wherein the message contains a response to the request for information regarding the benefit; and
  transmitting the message to the communication device associated with at least one of the employee, a benefit beneficiary, the second employer, and a benefit administrator, wherein the message is transmitted to the communication device via, on, or over, at least one of the Internet and the World Wide Web.

167. A computer-implemented method, comprising:
  storing or processing information regarding a benefit provided to an employee pursuant to an employee benefit relationship between the employee and a benefit provider, wherein the benefit is at least one of a health insurance benefit, a disability insurance benefit, and a life insurance benefit, and further wherein the employee benefit relationship is established pursuant to or during a first employment relationship between the employee and a first employer;
  storing or processing information for providing or maintaining the benefit provided to the employee pursuant to the employee benefit relationship pursuant to or during a second employment relationship between the employee and a second employer, wherein the second employment relationship is a current employment relationship, wherein the benefit provided pursuant to the employee benefit relationship is paid for or provided at least in part by the second employer in or pursuant to the second employment relationship and is included in employee benefits provided to the employee by the second employer;
  receiving a request for the benefit or a claim for the benefit, wherein the benefit is the benefit provided pursuant to the employee benefit relationship which is paid for or provided at least in part by the second employer in or pursuant to the second employment relationship and which is included in employee benefits provided to the employee by the second employer;
  processing the request for the benefit or the claim for the benefit with a processing device, wherein the processing device is a computer or a computer system which is accessed via, on, or over, at least one of the Internet and the World Wide Web or which operates on or over at least one of the Internet and the World Wide Web;
  generating a message in response to the processing of the request for the benefit or the claim for the benefit, wherein the message contains a response to the request for the benefit or the claim for the benefit; and
  transmitting the message to a communication device associated with at least one of the employee, a benefit beneficiary, the second employer, and a benefit administrator, wherein the message is transmitted to the communication device via, on, or over, at least one of the Internet and the World Wide Web.

168. The computer-implemented method of claim 167, further comprising:
  receiving a request for benefit information;
  processing the request for benefit information;
  generating a second message in response to the request for benefit information; and
  transmitting the second message to the communication device.

169. The computer-implemented method of claim 167, wherein the message contains information indicating that the benefit requested in the request for the benefit or the claim for the benefit is provided or will be provided.

170. The computer-implemented method of claim 167, further comprising:
providing the benefit requested or claimed in the request for the benefit or the claim for the benefit.

171. The computer-implemented method of claim 167, further comprising:
processing information regarding a registration for the benefit or a second benefit or processing information regarding a subscription to the benefit or to a second benefit.

172. The computer-implemented method of claim 167, further comprising:
processing a request for a status of the request for the benefit or the claim for the benefit;
generating a second message in response to the request for a status of the request for the benefit or the claim for the benefit; and
transmitting the second message to the communication device.

173. The computer-implemented method of claim 167, wherein the message contains information regarding a providing of a health insurance benefit or a providing of a payment pursuant to a health insurance benefit.

174. The computer-implemented method of claim 167, wherein the message contains information regarding a providing of a disability insurance benefit or a providing of a payment pursuant to a disability insurance benefit.

175. The computer-implemented method of claim 167, further comprising:
processing information regarding a purchase of a second benefit or a change to the benefit or to a second benefit.

176. The computer-implemented method of claim 167, wherein the benefit is a health insurance benefit.

177. The computer-implemented method of claim 167, wherein the benefit is a disability insurance benefit.

178. The computer-implemented method of claim 167, wherein the benefit is a life insurance benefit.

179. The computer-implemented method of claim 167, wherein the message contains information regarding at least one of a health insurance benefit, a disability insurance benefit, a life insurance benefit, a pension benefit, a retirement benefit, an educational assistance benefit, a tuition reimbursement benefit, a credit union benefit, an employee discount program benefit, a buying service benefit, and a stock option benefit.

180. The computer-implemented method of claim 167, wherein the communication device is at least one of a personal computer, a laptop computer, a personal digital assistant, a telephone, a handheld computer, and a personal communication device.

181. The computer-implemented method of claim 167, wherein the communication device is a television or an interactive television.

182. The computer-implemented method of claim 167, wherein the communication device is a wireless device.

183. The computer-implemented method of claim 167, wherein the communication device is a kiosk.

184. The computer-implemented method of claim 167, wherein the computer-implemented method is also performed or utilized on or over an intranet.

185. The computer-implemented method of claim 167, wherein the processing device is at least one of a central processing unit, a computer in a network, a server computer, and an Internet server computer.

186. The computer-implemented method of claim 167, wherein the information regarding a benefit is at least one of automatically updated and updated in real-time.

187. The computer-implemented method of claim 167, wherein the employee is an independent contractor.

188. The computer-implemented method of claim 167, further comprising:
processing information regarding a purchase pursuant to an employee discount benefit or a buying service benefit.

189. The computer-implemented method of claim 167, further comprising:
processing information regarding a registration for a class or a course or processing information regarding a request for a tuition reimbursement.

190. The computer-implemented method of claim 167, further comprising:
processing information regarding at least one of a selection of a primary care provider, a request for a referral authorization for a specialist, a status of a health insurance claim, a purchase of a health insurance benefit, a change in a health insurance coverage, a status of a disability insurance claim, a purchase of a disability insurance benefit, a change in a disability insurance coverage, a status of a life insurance claim, a purchase of a life insurance benefit, and a change in a life insurance coverage.

191. The computer-implemented method of claim 167, further comprising:
processing information regarding at least one of a placing of an order with a goods provider or a service provider, a registration with a goods provider or a service provider, a subscription to a goods provider or a service provider, and a status of a pending order.

192. The computer-implemented method of claim 167, further comprising:
providing information to the second employer regarding a transaction between the employee or a second employee and at least one of a health insurance benefit provider, a disability insurance benefit provider, and a life insurance benefit provider.

193. The computer-implemented method of claim 167, wherein the processing device is linked to at least one of an employer computer, a health insurance provider computer, a disability insurance provider computer, a life insurance provider computer, a credit union or banking services provider computer, a pension benefit provider computer, a retirement benefit provider computer, and an employee discount provider computer.

194. The computer-implemented method of claim 167, further comprising:
storing information regarding at least one of a benefit, a benefit package, and a benefit pricing, provided by a benefit provider, and information regarding a requirement for a benefit or a need for a benefit associated with at least one of the second employer, the employee, and a second employee;
processing the information regarding the at least one of a benefit, a benefit package, and a benefit pricing, with the information regarding a requirement for a benefit or a need for a benefit;
identifying a benefit provider for providing at least one of a benefit and benefit information for the requirement for a benefit or for the need for a benefit;
generating a second message containing information regarding the benefit provider, wherein the second message contains information regarding at least one of a benefit, a benefit package, and a benefit pricing, provided by the benefit provider; and transmitting the second message to the communication device or to a second communication device associated with at least one of the second employer, the employee, and the second employee.

195. The computer-implemented method of claim 167, wherein the message contains a link or a hyperlink to a computer associated with the processing device or to a benefit provider computer.

196. The computer-implemented method of claim 167, further comprising:
storing information regarding an individual benefits account, wherein the individual benefits account exists independently of the previous employment relationship and the current employment relationship.

197. The computer-implemented method of claim 167, further comprising:
processing information for pooling employees from a plurality of employers to obtain employee benefits for the employees of the plurality of different employers.

198. The computer-implemented method of claim 167, further comprising:
providing information to a benefit provider regarding the employee or a second employee who has upgraded a benefit or utilized at least one of a benefit offer, an employee discount benefit, and a buying service benefit.

199. The computer-implemented method of claim 167, further comprising:
processing information for allowing the employee or a second employee to utilize monies or credits provided by the second employer to obtain an employee benefit from a benefit provider, or processing information for allowing the employee or a second employee to utilize funds provided by the second employer to make a payment to a benefit provider.

200. The computer-implemented method of claim 167, further comprising:
processing information for establishing or creating an individual benefits account, wherein the individual benefits account exists independently of the previous employment relationship and the current employment relationship, and further wherein the employee pays for or purchases a benefit in whole or in part with at least one of funds, monies, and credits, provided by the second employer.

201. The computer-implemented method of claim 167, wherein the message contains information regarding a providing of a life insurance benefit or providing a payment pursuant to a life insurance benefit.

202. The computer-implemented method of claim 167, further comprising:
transmitting at least one of a benefit request form, a benefit information request form, a claim submission form, and a claim status form, to the communication device or to a second communication device associated with the at least one of the employee, a benefit beneficiary, the second employer, and a benefit administrator.

203. The computer-implemented method of claim 167, wherein the message contains information regarding a providing of a pension benefit or a retirement benefit or a providing of a payment pursuant to a pension benefit or a retirement benefit.

204. The computer-implemented method of claim 167, wherein the message is contained in at least one of an electronic mail transmission, an electronic transmission, a facsimile transmission, a telephone call, a telephone message, a voice message, a pager message, and a beeper message.

205. The computer-implemented method of claim 167, further comprising:
utilizing at least one of an electronic power of attorney form, an electronic authorization, an electronic signature, and a digital signature, to file at least one of a medical claim form, a dental claim form, a healthcare claim form, an insurance claim form, a financial transaction form, a financial claim form, a goods order form or a service order form, and a benefit request form.

206. The computer-implemented method of claim 167, wherein the message is transmitted to the communication device in real-time.

207. The computer-implemented method of claim 167, further comprising:
effectuating a payment pursuant to the benefit in response to the request for the benefit or the claim for the benefit.

208. The computer-implemented method of claim 167, wherein the computer-implemented method is performed or utilized via, on, or over, a cable television network.

209. The computer-implemented method of claim 167, wherein the request for the benefit or the claim for the benefit is transmitted from the communication device.

210. The computer-implemented method of claim 167, further comprising:
storing information regarding an individual benefits account, wherein the individual benefits account is utilized by the employee to retain a benefit with a benefit provider independently of the previous employment relationship and the current employment relationship.

211. The computer-implemented method of claim 167, further comprising:
storing at least one of vacation time benefit information, personal time benefit information, sick time benefit information, credit union benefit information, educational assistance benefit information, tuition reimbursement benefit information, employee discount benefit information, and buying service benefit information, wherein the message contains information regarding a providing of at least one of a vacation time benefit, a personal time benefit, a sick time benefit, a credit union benefit, an educational assistance benefit, a tuition reimbursement benefit, an employee discount benefit, and a buying service benefit.

212. The computer-implemented method of claim 167, further comprising:
transmitting information regarding at least one of a change to a benefit, a change to a benefit account, an activity regarding a benefit account, an offering of a benefit, a posting of an offer to sell a benefit, an advertisement for a benefit, a posting of benefit information, a payment to a deferred income savings account or a pension account, and a payment of a benefit claim.

213. A computer-implemented method, comprising:
storing or processing information regarding a benefit provided to an employee pursuant to an employee benefit relationship between the employee and a benefit provider, wherein the benefit is at least one of a health insurance benefit, a disability insurance benefit, and a life insurance benefit, and further wherein the employee benefit relationship is established pursuant to or during a first employment relationship between the employee and a first employer;

storing or processing information for providing or maintaining the benefit provided to the employee pursuant to the employee benefit relationship pursuant to or during a second employment relationship between the employee and a second employer, wherein the second employment relationship is a current employment relationship, wherein the benefit provided pursuant to the employee benefit relationship is paid for or provided at least in part by the second employer in or pursuant to the second employment relationship and is included in employee benefits provided to the employee by the second employer;

receiving a request for the benefit or a claim for the benefit, wherein the benefit is the benefit provided pursuant to the employee benefit relationship which is paid for or provided at least in part by the second employer in or pursuant to the second employment relationship and which is included in employee benefits provided to the employee by the second employer, and further wherein the request for the benefit or a claim for the benefit is transmitted from a communication device associated with at least one of the employee, a benefit beneficiary, the second employer, and a benefit administrator;

processing the request for the benefit or the claim for the benefit with a processing device, wherein the processing device is a computer or a computer system which is accessed via, on, or over, at least one of the Internet and the World Wide Web or which operates on or over at least one of the Internet and the World Wide Web;

generating a message in response to the processing of the request for the benefit or the claim for the benefit, wherein the message contains a response to the request for the benefit or the claim for the benefit; and transmitting the message to the communication device associated with at least one of the employee, a benefit beneficiary, the second employer, and a benefit administrator, wherein the message is transmitted to the communication device via, on, or over, at least one of the Internet and the World Wide Web.

214. The computer-implemented method of claim 213, further comprising:

storing information regarding an individual benefits account, wherein the individual benefits account is utilized by the employee to retain a benefit with a benefit provider independently of the previous employment relationship and the current employment relationship.

215. The computer-implemented method of claim 213, wherein the message contains information regarding a providing of at least one of a health insurance benefit, a disability insurance benefit, a life insurance benefit, a pension benefit, a retirement benefit, a vacation time benefit, a personal time benefit, a sick time benefit, an educational assistance benefit, a tuition reimbursement benefit, a credit union benefit, an employee discount program benefit, a buying service benefit, or a providing of a payment pursuant to at least one of a health insurance benefit, a disability insurance benefit, a life insurance benefit, a pension benefit, a retirement benefit, an educational assistance benefit, a tuition reimbursement benefit, and a credit union benefit.

216. A computer-implemented method, comprising:

storing information regarding a request by an employee or a benefit beneficiary to be notified regarding at least one of a posting of an offering of a benefit and a posting of an offer to sell a benefit or a benefit package, wherein the benefit or the benefit package is not available to the employee or the benefit beneficiary in or pursuant to an employment relationship prior to the at least one of a posting of an offering of a benefit and a posting of an offer to sell a benefit or a benefit package;

detecting the at least one of a posting of an offering of a benefit and a posting of an offer to sell a benefit or a benefit package, wherein the at least one of a posting of the offering of a benefit and a posting of an offer to sell a benefit or a benefit package is automatically detected by a processing device in response to the request by an employee or a benefit beneficiary to be notified regarding the at least one of a posting of an offering of a benefit and a posting of an offer to sell a benefit or a benefit package;

generating a first message containing information regarding the at least one of a posting of an offering of a benefit and a posting of an offer to sell a benefit or a benefit package, wherein the first message is automatically generated by the processing device upon the automatic detection of the at least one of a posting of an offering of a benefit and a posting of an offer to sell a benefit or a benefit package;

transmitting the first message to a first communication device associated with the employee or the benefit beneficiary;

receiving a second message transmitted from the first communication device or transmitted from a second communication device associated with the employee or the benefit beneficiary, wherein the second message contains information regarding a request to enroll the employee or the benefit beneficiary in the benefit or in the benefit package; and enrolling the employee or the benefit beneficiary in the benefit or the benefit package.

217. The computer-implemented method of claim 216, wherein the first message is transmitted to the communication device in real-time.

218. The computer-implemented method of claim 216, wherein the first communication device is at least one of a personal computer, a laptop computer, a personal digital assistant, a telephone, a handheld computer, and a personal communication device.

219. The computer-implemented method of claim 216, wherein the first communication device is a television or an interactive television.

220. The computer-implemented method of claim 216, wherein the first communication device is a wireless communication device.

221. The computer-implemented method of claim 216, wherein the first message is transmitted to the first communication device via, on, or over, at least one of the Internet and the World Wide Web.

222. The computer-implemented method of claim 216, wherein the first message is also transmitted to the first communication device via, on, or over, an intranet.

223. The computer-implemented method of claim 216, wherein information regarding the at least one of a posting of an offering of a benefit and a posting of an offer to sell a benefit or a benefit package is at least one of automatically updated and updated in real-time.

224. The computer-implemented method of claim 216, further comprising:

processing information regarding at least one of a purchase of a health insurance benefit, a change in a health insurance coverage, a purchase of a disability insurance benefit, a change in a disability insurance coverage, a purchase of a life insurance benefit, and a change in a life insurance coverage.

225. The computer-implemented method of claim 216, further comprising:
processing information regarding at least one of an allocation of pension funds among investment vehicles or options, a changing of an employee pension plan contribution, a filing of a pension benefit claim, a determination of a status of a pending pension benefit claim, an allocation of retirement funds among investment vehicles or options, and a changing of a contribution to a retirement account.

226. The computer-implemented method of claim 216, wherein the first message is contained or transmitted in at least one of a facsimile transmission, a telephone call, a telephone message, a voice message, a pager message, and a beeper message.

227. The computer-implemented method of claim 216, wherein the first message contains a link or a hyperlink to a computer associated with the processing device or to a benefit provider computer.

228. The computer-implemented method of claim 216, further comprising:
processing employee benefit information, wherein the employee benefit information comprises information regarding an employee benefit associated with an employee, wherein the employee benefit exists from a previous employment relationship with a first employer and is maintained by the employee in a current employment relationship with a second employer, wherein the employee benefit from the previous employment relationship is paid for or provided at least in part by the second employer pursuant to the current employment relationship with the second employer and is included in employee benefits provided to the employee by the second employer, and further wherein the employee benefit information comprises information regarding an individual benefits account, wherein the individual benefits account is utilized by the individual to retain a benefit with a benefit provider independently of an employment relationship.

229. The computer-implemented method of claim 216, further comprising:
storing information regarding at least one of a benefit, a benefit package, and a benefit pricing, provided by the benefit provider, and information regarding a requirement for a benefit or a need for a benefit associated with the employer or the employee;
processing the information regarding the at least one of a benefit, a benefit package, and a benefit pricing, with the information regarding a requirement for a benefit or a need for a benefit;
identifying a benefit provider for providing at least one of a benefit and benefit information for the requirement for a benefit or for the need for a benefit;
generating a third message containing information regarding the benefit provider, wherein the third message contains information regarding at least one of a benefit, a benefit package, and a benefit pricing, provided by the benefit provider; and
transmitting the third message to the first communication device.

230. The computer-implemented method of claim 216, wherein the first communication device is a personal computer or a laptop computer.

231. The computer-implemented method of claim 216, wherein the first communication device is a personal digital assistant.

232. The computer-implemented method of claim 216, wherein the first message is contained in an electronic mail message or transmitted in an electronic mail message.

233. A computer-implemented method, comprising:
storing information regarding a request by a benefit provider to be notified regarding a posting by an employee or a benefit beneficiary of at least one of a need, a request, and a requirement, to buy or to obtain a benefit or a benefit package, wherein the benefit or the benefit package is not available to the employee or the benefit beneficiary in or pursuant to an employment relationship at the time of the posting of the at least one of a need, a request, and a requirement, to buy or to obtain a benefit or a benefit package;
detecting the posting by an employee or a benefit beneficiary of at least one of a need, a request, and a requirement, to buy or to obtain a benefit or a benefit package, wherein the posting of at least one of a need, a request, and a requirement, to buy or to obtain a benefit or a benefit package is automatically detected by a processing device in response to the request by a benefit provider to be notified regarding a posting by an employee or a benefit beneficiary of at least one of a need, a request, and a requirement, to buy or to obtain a benefit or a benefit package;
generating a message containing information regarding the posting of at least one of a need, a request, and a requirement, to buy or to obtain a benefit or a benefit package, wherein the message is automatically generated by the processing device upon the automatic detection of the posting of at least one of a need, a request, and a requirement, to buy or to obtain a benefit or a benefit package;
transmitting the message to a communication device associated with the benefit provider; and
enrolling the employee or the benefit beneficiary in the benefit or the benefit package.

234. The computer-implemented method of claim 233, wherein the message is transmitted to the communication device in real-time.

235. The computer-implemented method of claim 233, wherein the message is transmitted to the communication device via, on, or over, at least one of the Internet and the World Wide Web.

236. The computer-implemented method of claim 233, wherein the message is also transmitted to the communication device via, on, or over, an intranet.

237. The computer-implemented method of claim 233, wherein the information regarding the posting by an employee or a benefit beneficiary of at least one of a need, a request, and a requirement, to buy or to obtain a benefit or a benefit package is at least one of automatically updated and updated in real-time.

238. The computer-implemented method of claim 233, further comprising:
processing information regarding at least one of a purchase of a health insurance benefit, a change in a health insurance coverage, a purchase of a disability insurance benefit, a change in a disability insurance coverage, a purchase of a life insurance benefit, and a change in a life insurance coverage.

* * * * *

UNITED STATES PATENT AND TRADEMARK OFFICE
CERTIFICATE OF CORRECTION

PATENT NO.        : 7,305,347 B1                                        Page 1 of 1
APPLICATION NO.   : 09/391335
DATED             : December 4, 2007
INVENTOR(S)       : Raymond Anthony Joao It is certified that error appears in the above-identified patent and that said Letters Patent is hereby corrected as shown below:

Col. 36, line 59, delete "a" before "the first process-".

Col. 46, line 51, insert "," after "information".

Col. 52, line 56, insert "," after "information".

Col. 54, line 15, insert "," after "information".

Col. 55, line 41, delete "a" before "the first".

Col. 55, line 44, insert "," after "information".

Col. 57, line 7, insert "," after "employee benefits information".

Signed and Sealed this

Twenty-sixth Day of February, 2008

JON W. DUDAS
*Director of the United States Patent and Trademark Office*